US008868225B2

(12) United States Patent
Lee et al.

(10) Patent No.: US 8,868,225 B2
(45) Date of Patent: Oct. 21, 2014

(54) SERVER FOR INTEGRATED PHARMACEUTICAL ANALYSIS AND REPORT GENERATION SERVICE, METHOD OF INTEGRATED PHARMACEUTICAL MANUFACTURING AND RESEARCH AND DEVELOPMENT NUMERICAL ANALYSIS, AND COMPUTER READABLE RECORDING MEDIUM

(75) Inventors: Yung-Jin Lee, Taoyuan (TW);
Ching-Feng Wang, Taoyuan (TW);
Hung-Liang Chen, Taoyuan (TW);
Ju-Min Chiu, Taoyuan (TW)

(73) Assignee: Taiwan Biotech Co., Ltd., Taoyuan (TW)

( * ) Notice: Subject to any disclaimer, the term of this patent is extended or adjusted under 35 U.S.C. 154(b) by 242 days.

(21) Appl. No.: 13/102,818

(22) Filed: May 6, 2011

(65) Prior Publication Data
US 2011/0276161 A1 Nov. 10, 2011

(30) Foreign Application Priority Data
May 7, 2010 (TW) ................................ 99114711 A

(51) Int. Cl.
G06F 19/00 (2011.01)
G06Q 50/22 (2012.01)
G06Q 10/10 (2012.01)

(52) U.S. Cl.
CPC ................ *G06Q 10/10* (2013.01); *G06Q 50/22* (2013.01)
USPC .............................. 700/97; 700/100; 700/103

(58) Field of Classification Search
None
See application file for complete search history.

(56) References Cited

U.S. PATENT DOCUMENTS

| 6,813,615 | B1* | 11/2004 | Colasanti et al. ............... 706/46 |
| 7,379,783 | B2 | 5/2008 | Popp |
| 7,379,784 | B2 | 5/2008 | Popp |
| 7,392,107 | B2 | 6/2008 | Popp |
| 7,471,991 | B2 | 12/2008 | Popp |
| 7,706,915 | B2* | 4/2010 | Mohapatra et al. ........... 700/231 |
| 7,799,273 | B2 | 9/2010 | Popp |

(Continued)

*Primary Examiner* — Sean Shechtman
(74) *Attorney, Agent, or Firm* — McDonnell Boehnen Hulbert & Berghoff LLP

(57) ABSTRACT

A web-based tool (as a server) for integrated pharmaceutical analysis and report generation service is provided in the present invention. The server can be used for numerical analysis and report generation for pharmaceutical manufacturing, research and development, and has advantages such as simple operation, complicated but fast calculation and professional report generation, and high accuracy. The server includes at least one pharmaceutical manufacturing and research and development numerical analysis system configured to perform different pharmaceutical manufacturing and research and development numerical analyses and generate different reports. Each of the at least one pharmaceutical manufacturing and research and development numerical analysis system includes an input module configured to receive, via a user interface, at least one of a template file and a backup file previously output by the server as at least one input file, wherein the at least one input file includes a plurality of data fields to provide corresponding data; at least one calculation module, each configured to execute a built-in pharmaceutical manufacturing and research and development numerical analysis calculation program, thereby automatically performing a pharmaceutical manufacturing and research and development numerical analysis calculation on at least one of the data of the at least one input file and on-line filled data; and an output module configured to generate at least one of a backup file and a report file as at least one output file based on the result of the pharmaceutical manufacturing and research and development numerical analysis calculation performed by the at least one calculation module and provide the at least one file via the user interface.

35 Claims, 17 Drawing Sheets

(56) References Cited

U.S. PATENT DOCUMENTS

| | | | |
|---|---|---|---|
| 2002/0095399 A1* | 7/2002 | Devine et al. ..................... 707/1 |
| 2003/0050825 A1* | 3/2003 | Gallivan et al. ................. 705/10 |
| 2003/0150908 A1* | 8/2003 | Pokorny et al. ............... 235/375 |
| 2004/0006403 A1* | 1/2004 | Bognanno .................... 700/109 |
| 2004/0019435 A1* | 1/2004 | Winfield et al. ................ 702/22 |
| 2004/0230592 A1* | 11/2004 | Fischer et al. ............... 707/100 |
| 2005/0038673 A1* | 2/2005 | Stookey et al. ................... 705/2 |
| 2005/0197786 A1* | 9/2005 | Kataria et al. .................. 702/19 |
| 2005/0288808 A1* | 12/2005 | Lopez et al. .................... 700/97 |
| 2006/0129828 A1* | 6/2006 | Shi ................................ 713/182 |
| 2007/0050070 A1* | 3/2007 | Strain et al. .................... 700/99 |
| 2007/0288114 A1* | 12/2007 | Popp ............................ 700/110 |
| 2008/0016116 A1* | 1/2008 | Tarr ........................... 707/104.1 |
| 2009/0254377 A1* | 10/2009 | Steen et al. ...................... 705/3 |
| 2010/0100214 A1* | 4/2010 | MacDonald ................... 700/97 |

\* cited by examiner

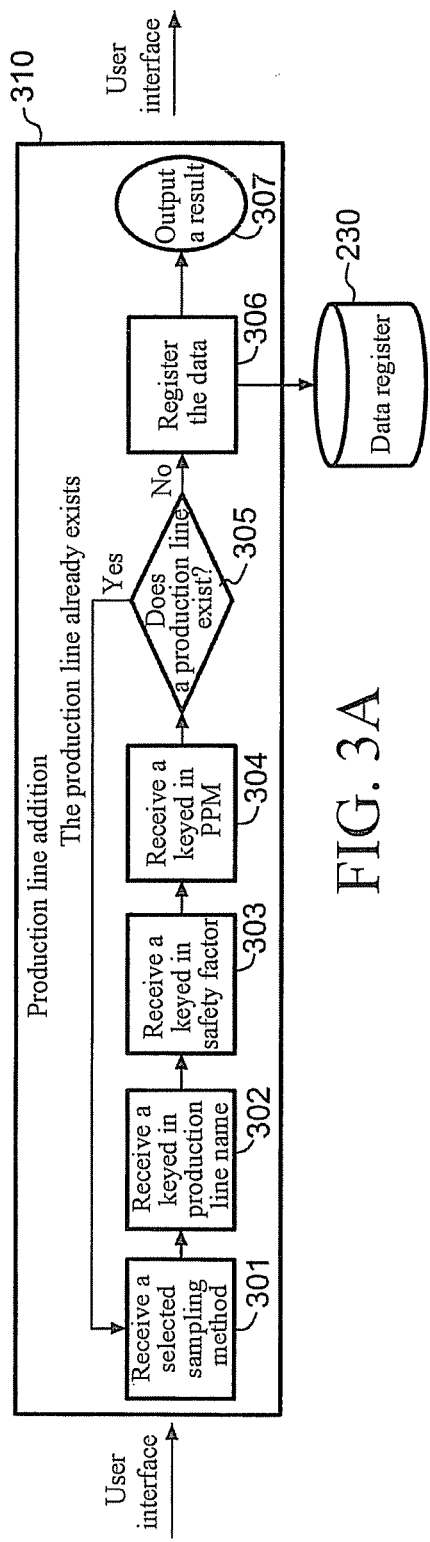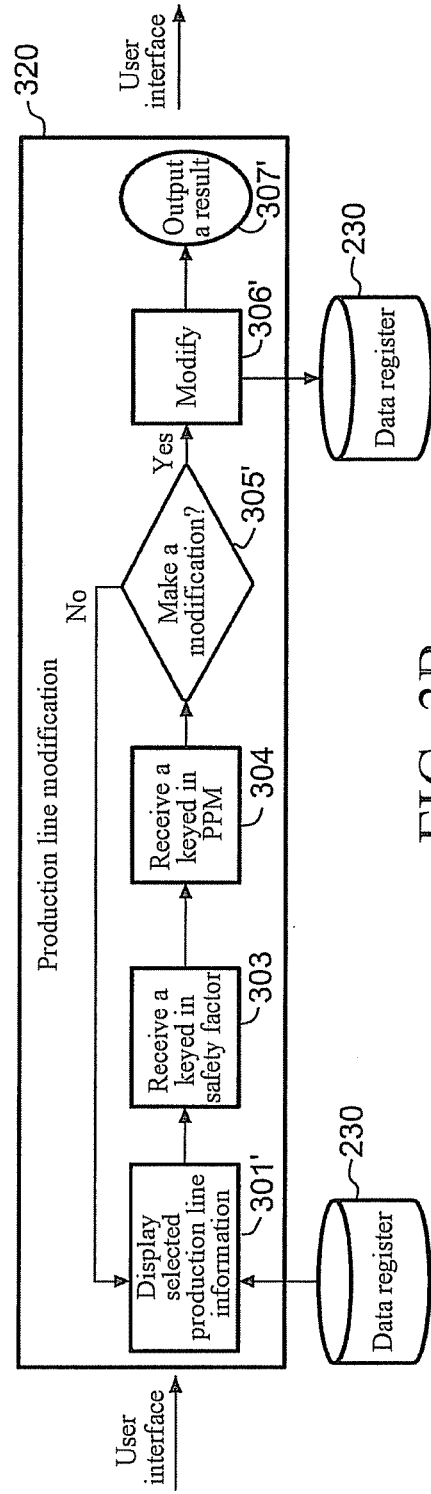
FIG. 3A
FIG. 3B

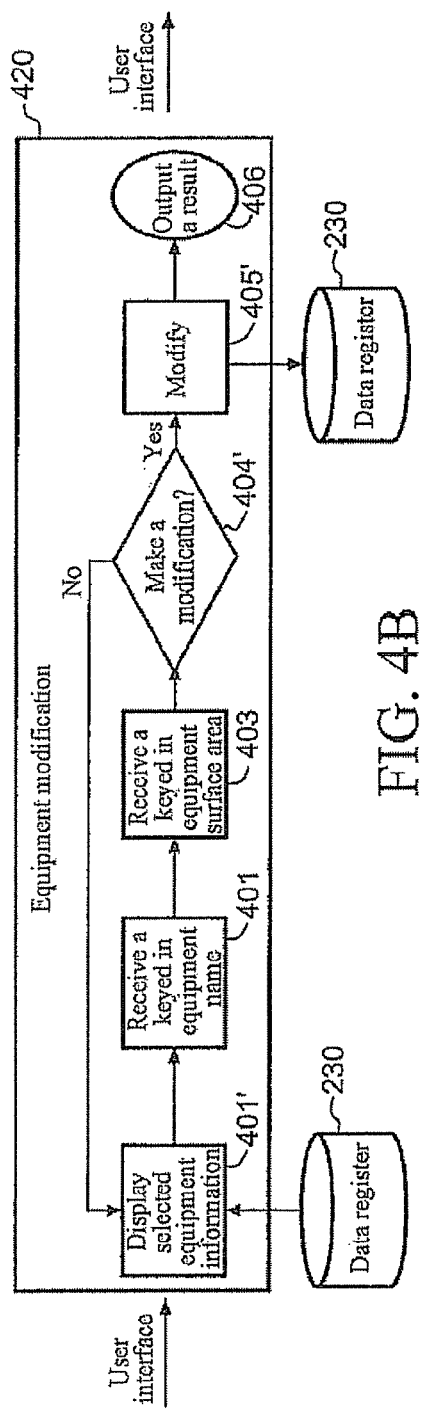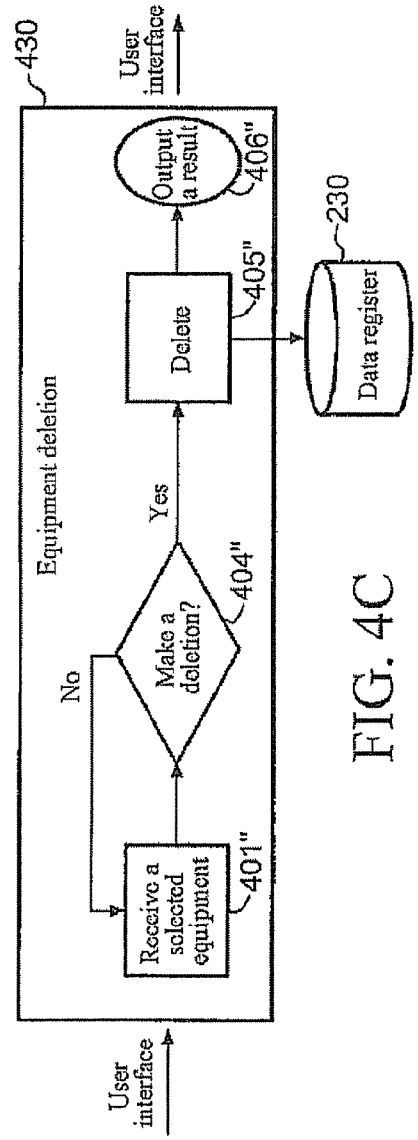
FIG. 4B
FIG. 4C

SERVER FOR INTEGRATED PHARMACEUTICAL ANALYSIS AND REPORT GENERATION SERVICE, METHOD OF INTEGRATED PHARMACEUTICAL MANUFACTURING AND RESEARCH AND DEVELOPMENT NUMERICAL ANALYSIS, AND COMPUTER READABLE RECORDING MEDIUM

BACKGROUND OF THE INVENTION

1. Field of the Invention

The present invention relates to pharmaceutical manufacturing and research and development relevant numerical analysis and report generation, and more particularly to a server for integrated pharmaceutical analysis and report generation service and a method thereof.

2. Description of the Prior Art

Conventionally, when pharmaceutical manufacturing and research and development-related numerical analysis and report generation is desired, the tools available to the user are always limited to commercially available common statistical application software packages, such as SAS (SAS Institutes), Statistical Package for the Social Science (SPSS), and Residue. Although such software packages have the benefit of presenting calculation results immediately without being limited by the network speed, numerous disadvantages exist.

For example, the problem of platform compatibility and software compatibility often arises, because such software generally can only be installed on a MICROSOFT® operating platform, but the same set of software cannot be installed in a new MICROSOFT® operating system environment (for example, WINDOWS 7®) when the operating system is updated. In addition, one by one installation of stand-alone software takes a long time, and the software can only be operated on a specific computer installed with the software, which limits the use to a specific space, and thus cannot meet the requirements for cross-regional and cross-border use.

Moreover, the operation process of such software is often troublesome. The reason is that the use interface function of such software is usually divided and hidden in different sub-window functional menu items, so the user cannot gain an overall view of all the functions at a glance, and may even need to use special program instructions in order to display an interface for input, which is rather inconvenient. In addition, special program syntax is needed to perform data calculation and report generation, which is not easy so the user needs to refer to a large number of instruction manuals. Further, such software packages generally divide a numerical calculation into many steps that may each require the user to fill in different numerical values or manually select a calculation mode, so the complete calculation often takes a lot of time to complete.

Furthermore, such software packages are not designed for pharmaceutical manufacturing and research and development numerical analysis, so new applications will cause new problems. The reason is that the new applications do not conform to the original requirements and purpose of the design, so a software package often cannot provide sufficient analysis calculation, and the entire calculation often can only be accomplished by using several software packages. In short, the user him/herself must add or develop multiple sets of separate software tools. Since different software packages are used differently, the user must learn to use each with its own complex and professional tools. In addition, the user has to assign the calculation work to different software and manually integrate the calculation results from different tools, so as to obtain the finally calculation. This is costly in terms of money, time, and man power, and too much manual intervention in the operation is also likely to cause omissions or errors in some processes.

Another tool currently available for pharmaceutical manufacturing research and development numerical analysis calculation is spreadsheet computer software, such as MICROSOFT OFFICE EXCEL®, which is applicable to most numerical calculations. Compared with the above-mentioned software packages, EXCEL® has the advantage of easy acquisition in addition to the fast calculation and immediate presentation of results. However, EXCEL® is also not designed specifically for pharmaceutical manufacturing and research and development numerical analysis calculation, so human errors in, for example, field setting and formula input easily occur, and a lot of time and manpower are required for repeated checks. In addition, learning to use such software is also time-consuming. Another disadvantage of EXCEL® is that malicious programs such as Trojan horses or back doors are easily inserted therein.

SUMMARY OF THE INVENTION

In order to simplify the operating steps, the present invention successfully integrates the functions of heterogeneous software packages, so that the user can accomplish complete upload of raw data and correct report generation through simple steps. In a preferred embodiment, the present invention further provides a cross-regional and cross-border network integration platform, thereby providing the user with pharmaceutical manufacturing and research and development numerical analysis services wherever they are.

In particular, the present invention is directed to a server for integrated pharmaceutical analysis and report generation service, which can be used for pharmaceutical manufacturing and research and development related numerical analysis and report generation and has such advantages as simple operation, fast calculation, and high accuracy. The present invention is further directed to a method of integrated pharmaceutical manufacturing and research and development numerical analysis and a computer-readable recording medium using the same. In a preferred embodiment, the above system, method, and computer readable recording medium can be implemented at a network server side, thereby providing a cross-regional and cross-border integrated platform.

In an embodiment, the present invention provides a server for integrated pharmaceutical analysis and report generation service, which includes at least one pharmaceutical manufacturing and research and development numerical analysis system configured to perform different pharmaceutical manufacturing and research and development numerical analyses. Each of the at least one pharmaceutical manufacturing and research and development numerical analysis system includes: an input module configured to receive, via a user interface, at least one of a template file and a backup file previously generated by the pharmaceutical manufacturing and research and development numerical analysis system as at least one input file, wherein the at least one input file includes a plurality of data fields to provide corresponding data; at least one calculation module, configured to execute a built-in pharmaceutical manufacturing and research and development numerical analysis calculation program, thereby automatically performing a pharmaceutical manufacturing and research and development numerical analysis calculation on at least one of the data of the at least one input file and data entered online; and an output module, configured to generate at least one of a backup file and a report file as at least one output file based on the result of the pharmaceutical manufacturing and research and development numerical analysis calculation performed by the at least one calculation module, and provide the at least one output file via the user interface.

In another embodiment, the present invention provides a method of integrated pharmaceutical manufacturing and research and development numerical analysis method, which includes performing at least one pharmaceutical manufacturing and research and development numerical analysis procedure. Each of the at least one pharmaceutical manufacturing and research and development numerical analysis procedure includes: receiving, via a user interface, at least one of at least one template file and a backup file previously output by the pharmaceutical manufacturing and research and development numerical analysis procedure as at least one input file, wherein the at least one input file includes a plurality of data fields to provide corresponding data; executing a built-in numerical analysis calculation program, thereby automatically performing a pharmaceutical manufacturing and research and development numerical analysis calculation on at least one of the data of the at least one input file and the data entered online; and generating at least one of a backup file and a report file as at least one output file based on the result of the numerical analysis calculation, and providing the at least one output file via the user interface.

In another embodiment, the present invention provides a computer readable recording medium for storing multiple experimental data and calculation and analysis results.

BRIEF DESCRIPTION OF THE DRAWINGS

FIGS. 3A, 3B, and 3C are flow charts showing a production line addition procedure, a production line modification procedure, and a production line deletion procedure, respectively, according to specific embodiments;

FIGS. 4A, 4B, and 4C are flow charts showing an equipment addition procedure, an equipment modification procedure, and an equipment deletion procedure, respectively, according to specific embodiments;

DETAILED DESCRIPTION

Figure 1:
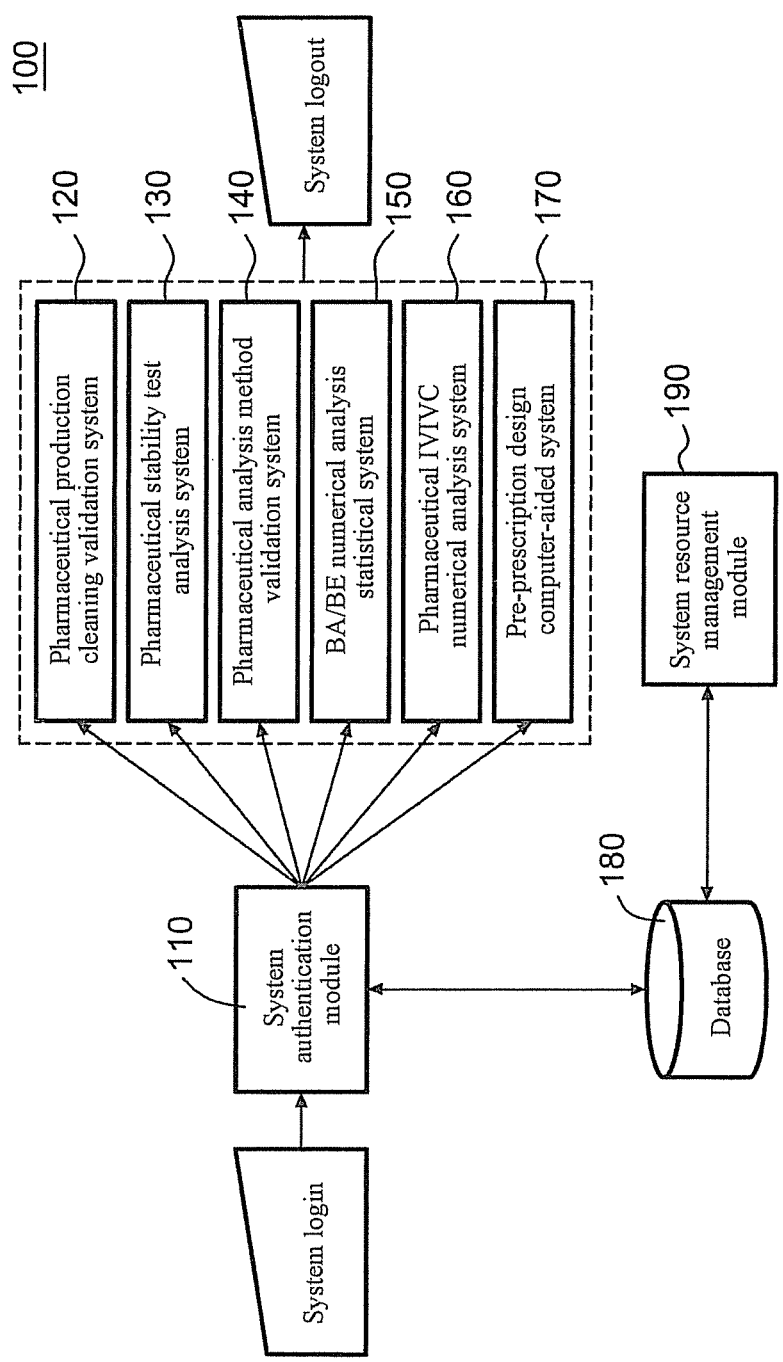
FIG. 1 is a schematic view of the structure of a server for integrated pharmaceutical analysis and report generation service according to an embodiment.

FIG. 1 is a schematic view of the structure of a server for integrated pharmaceutical analysis and report generation service 100 according to an embodiment, which can be used for pharmaceutical manufacturing and research and development related numerical analysis and report generation. Preferably, the server for integrated pharmaceutical analysis and report generation service 100 is a network server located at a server side. Man-machine interaction may be achieved between a user and the server for integrated pharmaceutical analysis and report generation service 100 via a user interface (not shown). When the server for integrated pharmaceutical analysis and report generation service 100 is implemented as a network server, the user interface may be a webpage interface located at a client.

As shown in FIG. 1, the server for integrated pharmaceutical analysis and report generation service 100 may mainly include a system authentication module 110 configured to authenticate the access right of a user logging in to the system. In addition, the server for integrated pharmaceutical analysis and report generation service 100 may further include at least one pharmaceutical manufacturing and research and development numerical analysis system 120-170 configured to perform different pharmaceutical manufacturing and research and development numerical analyses.

Specifically, the system authentication module 110 can perform identity authentication on the user logging into the system, for example, determine whether the user has valid access right and authority after receiving an account number and a password provided by the user (or an authentication code). In an embodiment, the user valid access right is limited (for example, through a purchase procedure) to one of the at least one pharmaceutical manufacturing and research and development numerical analysis system 120-170. In addition, the system authentication module 110 can also be configured to prevent repetitive logins with the same account number.

In an embodiment, the at least one pharmaceutical manufacturing and research and development numerical analysis system may be at least one of a pharmaceutical production cleaning validation system 120, a pharmaceutical stability test analysis system 130, a pharmaceutical analysis method validation system 140, a pharmaceutical bioavailability/bioequivalence (BA/BE) numerical analysis statistical system 150, a pharmaceutical in vitro/in vivo correlation (IVIVC) numerical analysis system 160, and a pre-prescription design computer-aided system 170.

The pharmaceutical BA/BB numerical analysis statistical system 150 is configured to perform relevant calculation and analysis of BA or BE tests on a pharmaceutical. The pharmaceutical IVIVC numerical analysis system 160 is configured to perform relevant calculation and analysis of in vitro dissolution and in vivo absorption on a pharmaceutical. The pre-prescription design computer-aided system 170 is configured to calculate the content of an active component of a pharmaceutical, thereby adjusting absorption and release rates of the active component. The pharmaceutical production cleaning validation system 120, the pharmaceutical stability test analysis system 130, and the pharmaceutical analysis method validation system 140 will each be illustrated in detail below.

The server for integrated pharmaceutical analysis and report generation service 100 may further include a database 180 configured to store relevant data of the access right of a user (for example, account number, password, and data of a pharmaceutical manufacturing and research and development numerical analysis system allowed to be used) and relevant data (for example, explanatory glossary) of the pharmaceutical manufacturing and research and development numerical analysis performed by the at least one pharmaceutical manufacturing and research and development numerical analysis system 120-170.

The server for integrated pharmaceutical analysis and report generation service 100 may further include a system resource management module 190 configured to manage at least one of the database 180, the at least one pharmaceutical manufacturing and research and development numerical analysis system 130-170, and a data register (not shown in FIG. 1). For example, after any pharmaceutical manufacturing and research and development numerical analysis system completes calculation and generates an output file, the system resource management module 190 can delete the data in the data register and at least one input file received by the pharmaceutical manufacturing and research and development numerical analysis system; once the user logs out, the system resource management module 190 can delete the output file in the data register and any remaining data, thereby ensuring the confidentiality and security of user data.

The respective detailed structures and operation processes of the pharmaceutical production cleaning validation system 120, the pharmaceutical stability test analysis system 130, and the pharmaceutical analysis method validation system 140 shown in FIG. 1 will be illustrated in detail below. The following illustration will it make clear that, when operating any one of the pharmaceutical production cleaning validation system 120, the pharmaceutical stability test analysis system 130, and the pharmaceutical analysis method validation system 140, the user only needs to input and store relevant data according to the input items in at least one template file and select a file to be calculated via the user interface for upload, and can easily acquire the calculated results and relevant expert suggestions via the user interface. The user can make proper arrangement for pharmaceutical manufacturing schedule of production lines in accordance with the suggestion.

Pharmaceutical Production Cleaning Validation System

It is well-know that equipment for manufacturing pharmaceuticals must be cleaned before use. This is mainly to avoid contamination and mixture between pharmaceuticals as well as contamination caused by improper cleaning or equipment maintenance or poor dust control system, for example, cross contamination between non-penicillin pharmaceuticals and penicillin pharmaceuticals or cross contamination between pharmaceuticals and steroids, cytotoxins, or hormones. For relevant provisions about cleaning validation, reference can be made to the Current Good Pharmaceutical Manufacturing Practices—Cleaning Validation Guidelines published by the Department of Health, Executive Yuan, Taiwan.

One of the applications of the pharmaceutical production cleaning validation system 120 in FIG. 1 is to assist in ensuring compliance with the foregoing Guidelines. The pharmaceutical production cleaning validation system 120 can perform a cleaning validation analysis calculation on each of a plurality of pharmaceuticals on at least one production line, and the calculation results can be provided to a user (for example, a pharmaceutical factory worker), so that the user can determine whether the equipment used in pharmaceutical manufacturing is cleaned according to a determined method without having to make complex calculations himself/herself, thereby ensuring that the residue of the previous batch of pharmaceuticals does not cross-contaminate the next batch of pharmaceuticals.

In an embodiment, the cleaning validation analysis calculation performed by the pharmaceutical production cleaning validation system 120 includes calculating the minimum allowable residual quantity values of a plurality of pharmaceuticals on each production line. In a preferred embodiment, the cleaning validation analysis calculation further includes screening an index pharmaceutical from the pharmaceuticals. In a more preferred embodiment, the cleaning validation analysis calculation further includes obtaining by analysis a suggested production schedule for the pharmaceuticals.

Figure 2:
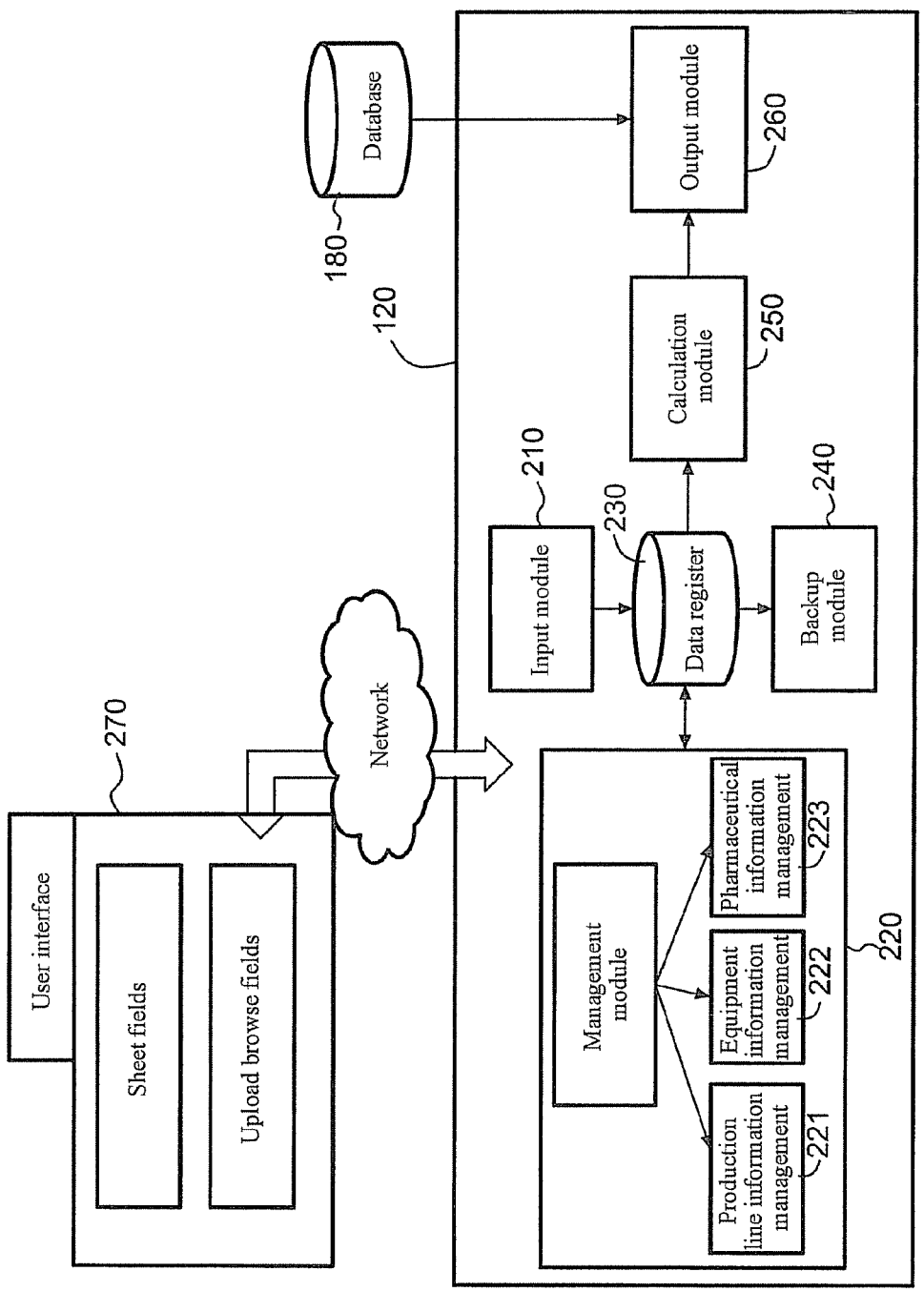
FIG. 2 is a schematic view the structure of a pharmaceutical production cleaning validation system according to an embodiment.

FIG. 2 is a schematic view of the structure of the pharmaceutical production cleaning validation system 120 according to an embodiment. As shown in FIG. 2, the pharmaceutical production cleaning validation system 120 may include an input module 210, a management module 220, and a data register 230 which are mainly responsible for receiving and registering data. The pharmaceutical production cleaning validation system 120 further includes a calculation module 250 and a backup module 240, which are mainly responsible for performing a cleaning validation analysis calculation and providing a backup of the received and registered data, respectively. In addition, the pharmaceutical production cleaning validation system 120 further includes an output module 260 mainly responsible for outputting results of the cleaning validation analysis calculation and the backup.

The above-mentioned data reception and storage, data processing and backup, and calculation result output will each be elaborated below to explain the detailed structure and operation process of the pharmaceutical production cleaning validation system 120, thereby highlighting its differences from and advantages over prior art.

First, the data receiving process may mainly be implemented by the input module 210, the management module 220, and the data register 230. Before the respective operation processes of the above components are illustrated, the form and content of the received data are first explained below.

The form of the received data may be at least one of at least one template file and the data entered online. The template file may include a plurality of data fields of designated items for a user to fill in corresponding data content. Preferably, the at least one template file can be provided (for example, by download) to the user, so that the user can directly input and modify the data. The data entered online can be used to make up for the insufficiency of data provided by the at least one input file or can directly replace the at least one input file, thereby improving the convenience and flexibility of use.

If the pharmaceutical production cleaning validation system 120 has previously output a backup file (to be explained later in the backup process) containing at least a part of the data of the input file or the data entered online, the backup file may also be selected as the input file, so that the user can also do without editing a template file, and may even not need to fill in data online (or only need to fill fewer data fields), thereby saving the time spent on editing the template file and providing data online.

In a specific embodiment, the content of the received data may include production line information, equipment information, and pharmaceutical information. Since the received data may be in different forms, the pharmaceutical production cleaning validation system 120 can receive an equipment template file or an equipment backup file containing partial or complete equipment information, and/or data entered online containing partial or complete equipment information, so as to obtain complete equipment information. Similarly, the pharmaceutical production cleaning validation system 120 can receive a pharmaceutical template file or a pharmaceutical backup file containing partial or complete pharmaceutical information, and/or data entered online containing partial or complete pharmaceutical information. The slight difference is that, instead of a complete file the pharmaceutical production cleaning validation system 120 can receive a production line backup file containing partial or complete equipment information and/or data entered online containing partial or complete equipment information. The production line information, equipment information, and product information are illustrated in detail below.

The production line information may include, for example, sampling method data, production line name data, safety factor data, and product residual limit data. Different sampling methods are employed in accordance with different equipment types to evaluate whether residues have been effectively eliminated after the equipment used in the pharmaceutical manufacturing process is cleaned. In an embodiment, the sampling method may be a swabbing method or a rinsing method, each of which is associated with a different calculation method and explanatory glossary. A safety factor may represent the maximum ratio of the amount of any pharmaceutical present in the maximum daily dose of a subsequent pharmaceutical to the minimum daily dose of the pharmaceutical for normal treatment in which the former does not exceed the latter. A product residual limit represents a lower limit of an allowable residual concentration of any pharmaceutical present in another pharmaceutical.

The equipment information may include, for example, at least one of equipment name data, equipment serial number data, and equipment surface area data.

The pharmaceutical information may include, for example, name of the pharmaceutical, name of the pharmaceutical active ingredient, content, weight solubility, cleaning level, production batch, minimum daily dose of an active ingredient, maximum daily dose of an active ingredient, toxicity level (for example, $LD_{50}$), total organic carbon (TOC), molecular weight of a pharmaceutical active ingredient, and other descriptive data.

Again as shown in FIG. 2, the management module 220 can perform, for example, production line information management 221, equipment information management 222, and pharmaceutical information management 223, respectively configured to manage processes of receiving production line information, equipment information, and pharmaceutical information, and temporarily store the data entered online in the data register 230. When the at least one input file is to be uploaded, the input module 210 can receive the at least one input file and process it by, for example filtering, recognition, decryption, and conversion, so as to correctly read the content thereof. The content read may also be stored in the data register 230.

The data register 230 is configured to register data associated with a user when the user logs in and remove the data associated with the user when the user logs out, so as to prevent the data associated with the user from being stolen.

The pharmaceutical production cleaning validation system 120 can receive the above data via a user interface 270. In an embodiment, the server for integrated pharmaceutical analysis and report generation service 100 is implemented as a network server located at a server side, and the user interface 270 is a webpage interface located at a client, i.e., an operation screen seen by the user. Since, as mentioned in the above, the received data may be in different forms, the operation screen can upload at least one of browse fields and sheet fields as a main constituent element thereof. The browse fields enable the user to upload the at least one input file, while the sheet fields enable the user to directly fill in data online.

Operation screens in the production line information management 221, the equipment information management 222, and the pharmaceutical information management 223 are each further illustrated below.

Regarding the production line information management 221, in an embodiment, the operation page is continuously a webpage sheet, and the user provides production line information by filling if in online without uploading any input file.

Operation screens of the equipment information management 222 and the pharmaceutical information management 223 are quite similar. In an embodiment, when the user initially has no equipment information/pharmaceutical information in the data register 230, the operation page is displayed as a first-stage file upload page. The user then can import and upload an edited equipment template file or a stored equipment backup file. Afterwards, the operation page is converted into a second-stage webpage sheet, so that the user can make up for the insufficient equipment/pharmaceutical information in the previous input file by filling in the data online without re-upload.

In view of the above, it is clear that, the process is quite simple for the user, because the user only needs to input and store relevant data under the guidance regarding input items in at least one template file, select a template file or a backup file to be analyzed and calculated for upload, or/and fill in data online in accordance with the sheet fields displayed on an operation screen.

Figure 3C:
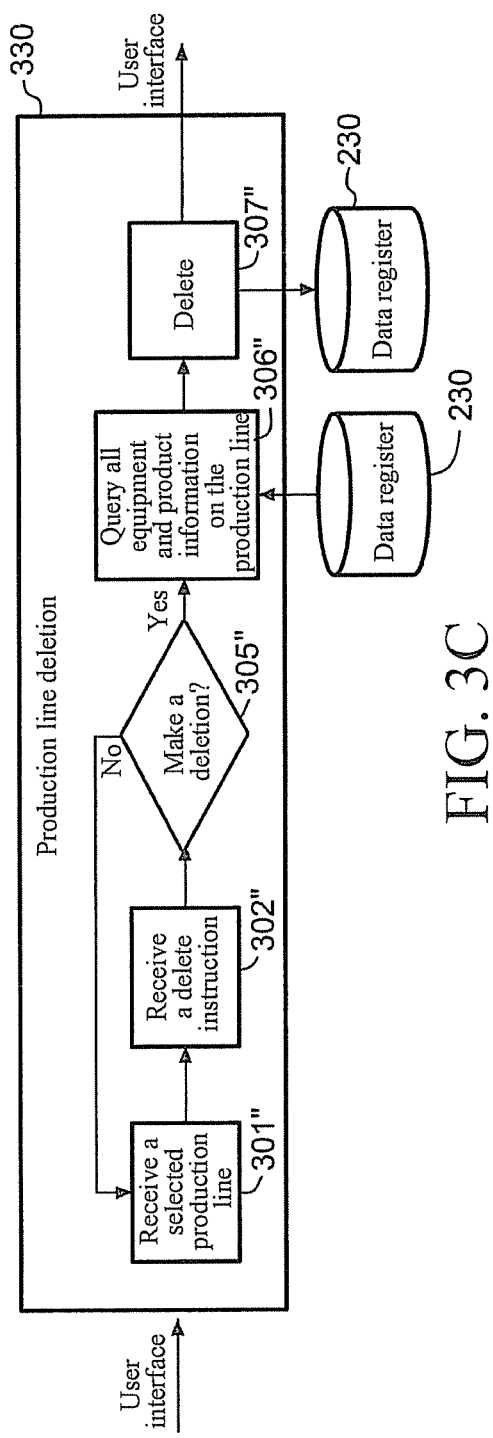

FIGS. 3A, 3B, and 3C are flow charts showing a production line addition procedure 310, a production line modification procedure 320, and a production line deletion procedure 330, respectively, in the production line information management 221 performed by the management module 220 according to specific embodiments. In the procedures 310, 320, and 330, the user interface 270 can display corresponding sheet fields for each step for the user to fill in data.

As shown in to FIG. 3A, the production line addition procedure 310 starts by receiving a selected sampling method (Step 301). The sampling method is, for example, a swabbing method or a rinsing method. Next, production line name data is received (Step 302). Next, a safety factor keyed in by the user is received (Step 303). The user may, for example, set the safety factor with reference to the values suggested in general cleaning validation documents. The user can not only employ a preset value, but also manually make a modification and input other values. In an embodiment, a preset value of the safety factor is 0.001. Next, a product residual limit keyed in by the user which has a unit of ppm (i.e., part per million) is received (Step 304). A preset value of the product residual limit may be, for example, 10 ppm. Reference can be made to Current Good Pharmaceutical Manufacturing Practices— Cleaning Validation Guidelines, which specifies that an amount of any pharmaceutical present in another pharmaceutical should not be greater than 10 ppm.

Next, whether a production line exists is determined (Step 305). If so, the process returns to Step 301 to add another production line; if not, the data received in Steps 301-304 are stored in the data register 230 (Step 306), and the user interface 270 then changes to display a result of the production line addition procedure 310 (Step 307).

As shown in FIG. 3B, the production line modification procedure 320 is substantially the same as the production line addition procedure 310 in FIG. 3A, and the difference mainly lies in that Steps 301 and 302 are replaced by Step 301', in which production line information is extracted from the data register 230 and displayed on the operation screen for the user to select a production line. Next, Steps 303 and 304 are performed likewise. Next, Step 305' is performed to determine whether to make a modification. If not, the process returns to Step 301'; if so, Step 306' is performed to modify the production line information stored in the data register 230 on the basis of the data received in Steps 303 and 304. Finally, the user interface 270 can change to display a result of the production line modification procedure 320 (Step 307').

As shown in FIG. 3C, in the production line deletion procedure 330, first, data of a production line selected to be deleted is received (Step 301"). Next, an instruction to delete is received (Step 302"). Next, whether to make a deletion is determined (Step 305"). If not, the process returns to Step 301"; if so, the process proceeds to Step 306", in which all equipment information and pharmaceutical information on the deleted production line are searched. Finally, the equipment and pharmaceutical information in the data register 230 associated with the production line is deleted together (Step 307").

Figure 4A:
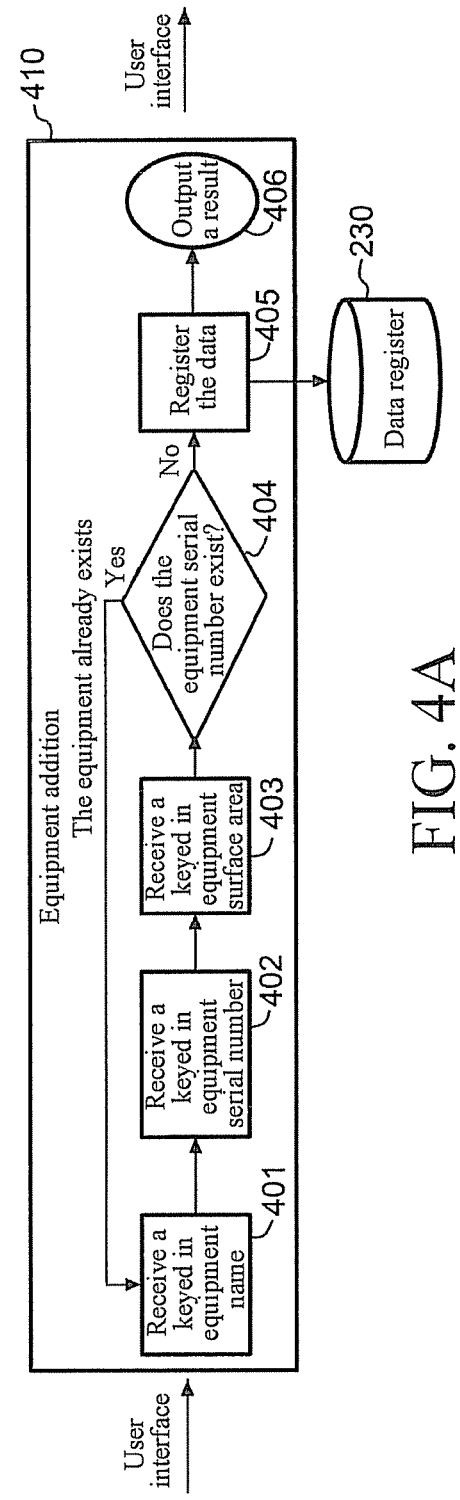

FIGS. 4A, 4B, and 4C are flow charts showing an equipment addition procedure 410, an equipment modification procedure 420, and an equipment deletion procedure 430, respectively, in the equipment information management 222 performed by the management module 220 according to specific embodiments.

As shown in FIG. 4A, Steps 401, 402, and 403 are performed (in an interchangeable order) to receive the data about a name, a serial number, and a surface area, respectively, of equipment. Next, whether the equipment exists is determined (Step 404). If so, the process returns to Step 401 to start to add another equipment; if not, the data received in Steps 401-403 is stored in the data register 230 (Step 405), and the user interface 270 can then change to display a result of the equipment addition procedure 410 (Step 406).

As shown in FIG. 4B, the equipment modification procedure 420 is substantially the same as the equipment addition procedure 410 in FIG. 4A, and the difference mainly lies in that the equipment modification procedure 420 starts with a Step 401', in which equipment information is extracted from the data register 230 and displayed on the operation screen for the user to select equipment. Next, Steps 401 and 403 are performed likewise. Next, Step 404' is performed to determine whether to make a modification. If not, the process returns to Step 401'; if so, Step 405' is performed to modify the equipment information stored in the data register 230 on the basis of the data received in Steps 401 and 403. Finally, the user interface 270 can change to display a result of the equipment modification procedure 420 (Step 406').

As shown in FIG. 4C, Steps 401", 404", and 405" are performed sequentially to select an equipment to be deleted, determine whether to make a deletion, and modify the equipment information stored in the data register 230, respectively. The user interface 270 can then change to display a result of the equipment deletion procedure 430 (Step 406").

Figure 5A:
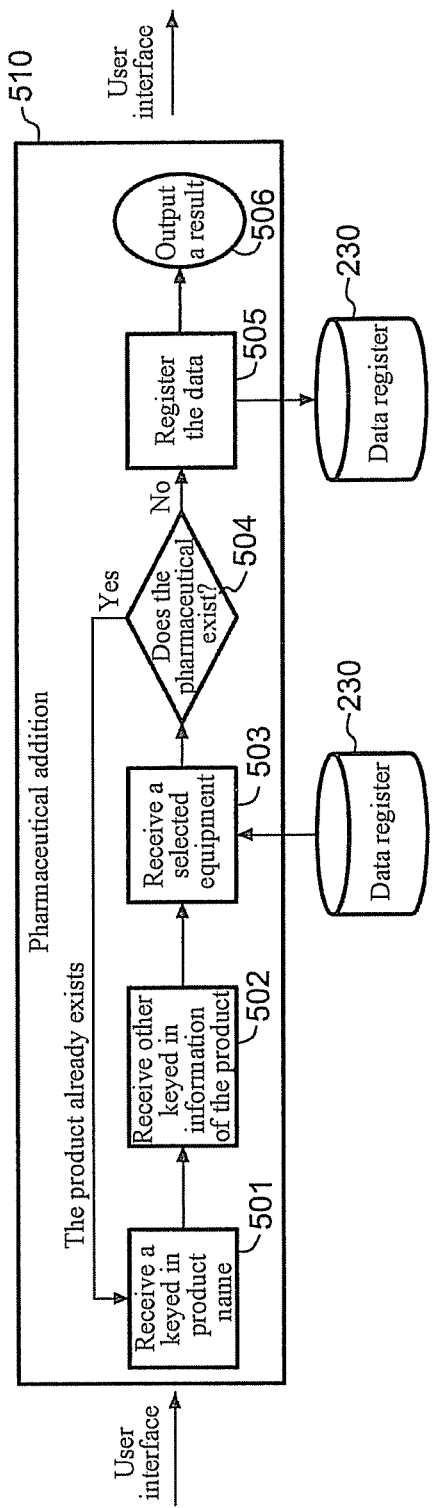
FIGS. 5A, 5B, and 5C are flow charts showing a pharmaceutical addition procedure, a pharmaceutical modification procedure, and a pharmaceutical deletion procedure, respectively, according to specific embodiments.
Figure 5B:
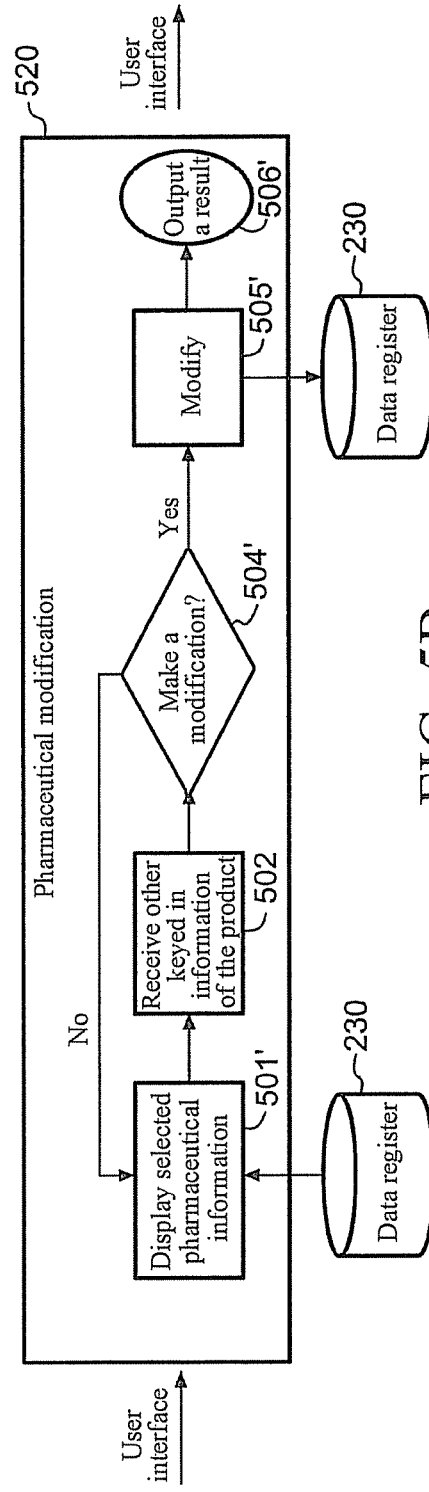
Figure 5C:
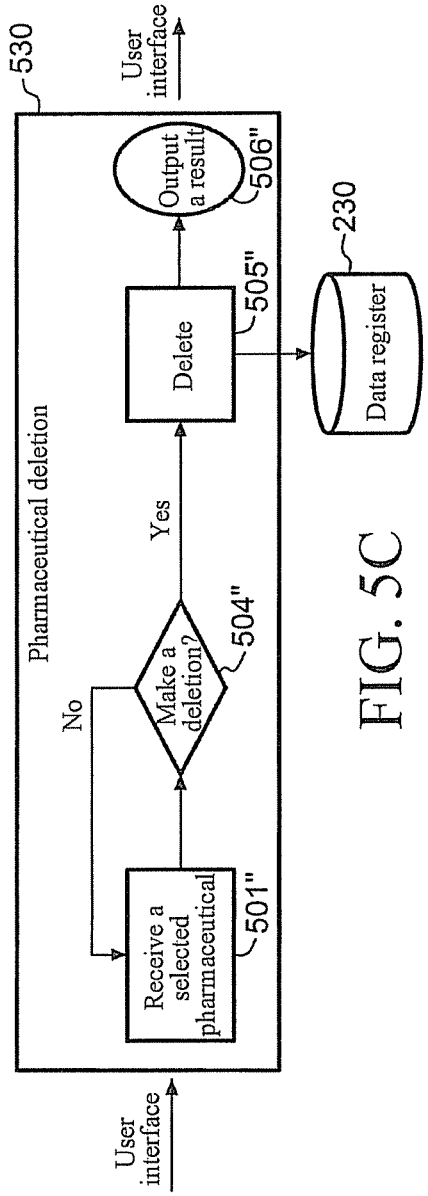

FIGS. 5A, 5B, and 5C are flow charts showing a pharmaceutical addition procedure 510, a pharmaceutical modification procedure 520, and a pharmaceutical deletion procedure 530, respectively, in the pharmaceutical information management 223 performed by the management module 220 according to specific embodiments.

As shown in FIG. 5A, Steps 501, 502, and 503 may be performed sequentially to receive the name of a pharmaceutical and other relevant data of the pharmaceutical, and access equipment data in the data register 230 associated with the pharmaceutical. Next, whether the pharmaceutical exists is determined (Step 504). If so, the process returns to Step 501 to add another pharmaceutical; if not, the data received in Steps 501-503 is stored in the data register 230 (Step 505). The user interface 270 can then display a result of the pharmaceutical addition procedure 510 (Step 506).

As shown in FIG. 5B, in the pharmaceutical modification procedure 520, first, pharmaceutical information is extracted from the data register 230 and displayed on the operation screen for the user to select a pharmaceutical (Step 501'). Next, other relevant data of the pharmaceutical is received (Step 502), whether to make a modification is determined (Step 504'), and the pharmaceutical information stored in the data register 230 is modified on the basis of the data received in Step 502 (505'). The user interface 270 can then change to display a result of the pharmaceutical modification procedure 520 (Step 506').

As shown in FIG. 5C, Steps 501", 504", and 505" are performed sequentially to respectively receive data of a pharmaceutical selected to be deleted, determine whether to make a deletion, and delete the pharmaceutical information stored in the data register 230, respectively. The user interface 270 can then change to display a result of the pharmaceutical deletion procedure 530 (Step 506").

Figure 6:
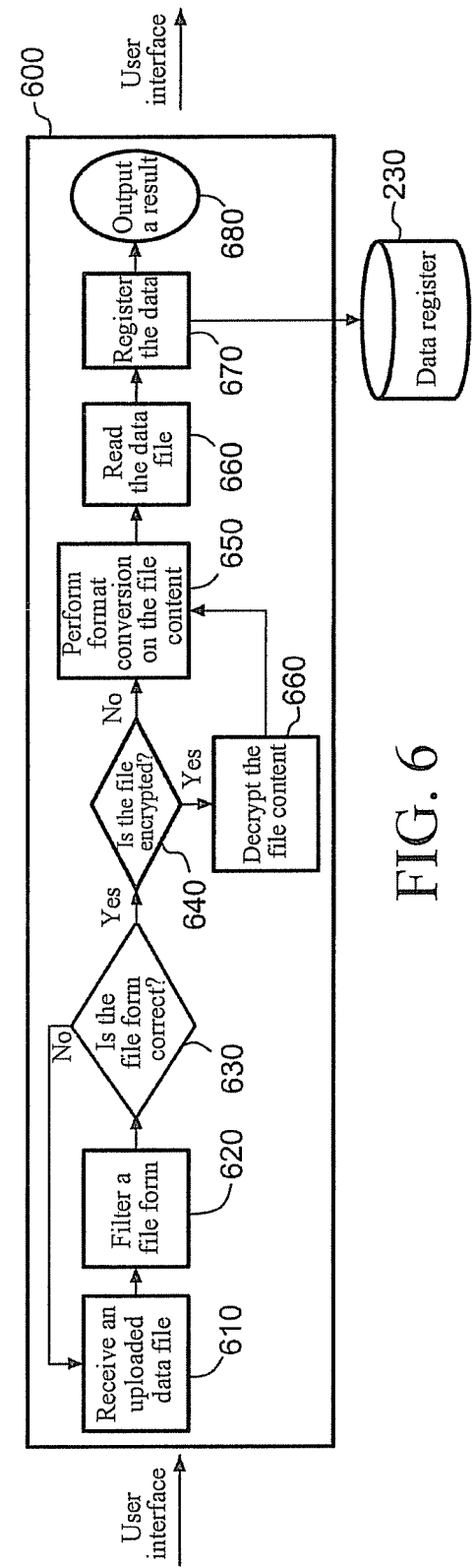
FIG. 6 is a flow chart of a file upload procedure performed by an input module according to a specific embodiment.

FIG. 6 is a flow chart of a file upload procedure 600 performed by the input module 210 according to a specific embodiment. As shown in FIG. 6, first, an uploaded input file is received (Step 610), and a format of the input file is filtered (Step 620). In an embodiment, only two formats, i.e., an input file (XLS) and an encrypted backup file (DES) are accepted. Next, it is recognized whether the file form is correct (Step 630). If not, the process returns to Step 610; if so, whether the input file is encrypted is determined (Step 640), for example, whether the input file is in the DES format may be identified. If not, format conversion is performed on the content of the input file (Step 650), for example, an XLS file may be converted into a pure text file (for example, in CSV format), thereby avoiding errors in subsequent reading of the file by a program; if so, the file content is decrypted (Step 660), for example, a DES file is converted into an XLS file, and then the process proceeds to Step 650. Next, the input file is read (Step 660), and read data is stored in the register 230 (Step 670). Optionally, a content format may further be detected to determine whether the file content includes incomplete or wrong data, such as the field for filling in numbers is filled in with Chinese characters or English words (not shown). Once the content format is wrong, the operation page is converted into an error message page to notify the user to re-import a file. Next, the user interface 270 can change to display a result of the file upload procedure (Step 680).

As shown in FIG. 2, after the above data is received and registered, data processing and backup processes may be performed, mainly implemented by the calculation module 250 and the backup module 240, respectively. The calculation module 250 can execute a built-in cleaning validation analysis calculation program, so as to access the data stored in the data register 230 and perform a cleaning validation analysis calculation on the data.

Meanwhile, the backup module 240 can back up at least a part of the data in the data register 230 as a backup file, and provide the backup file via the user interface 270.

In the process of performing the cleaning validation analysis calculation, the calculation module 250 can calculate minimum allowable residual quantity values between a plurality of pharmaceuticals on each production line on the basis of the accessed data. Moreover, the calculation module 250 can screen out an index pharmaceutical from the plurality of pharmaceuticals on each production line. In addition, the calculation module 250 can obtain by analysis a suggested production schedule for the plurality of pharmaceuticals on each production line.

Regarding the calculation of the minimum allowable residual quantity values between pharmaceuticals, for example, if 8 pharmaceuticals exist on a certain production line, the calculation module 250 can calculate a minimum allowable residual quantity value for any two pharmaceuticals, and thus can provide a total of 56 minimum allowable residual quantity values for the 8 pharmaceuticals. In addition, the pharmaceutical production cleaning validation system 120 can further sort out the lowest ones, for example, 5 or 10 values, in the 56 values.

Regarding the screening of the index pharmaceutical, in an embodiment, the calculation module 250 can screen the index pharmaceutical as a most difficult-to-clean pharmaceutical. In the process of screening the index pharmaceutical, the calculation module 250 can screen the index pharmaceutical according to at least one of a dissolution level, a cleaning level, and a toxicity level (for example, $LD_{50}$) of the pharmaceuticals.

Regarding the analysis of the suggested production schedule, in an embodiment, the calculation module 250 can further obtain by analysis a suggested production schedule on the basis of the calculated minimum allowable residual quantity values between the pharmaceuticals and the selected index pharmaceutical to assist in different considerations and determinations during the cleaning validation operation of the pharmaceutical factory, thereby avoiding the problem of pharmaceutical contamination.

Figure 7:
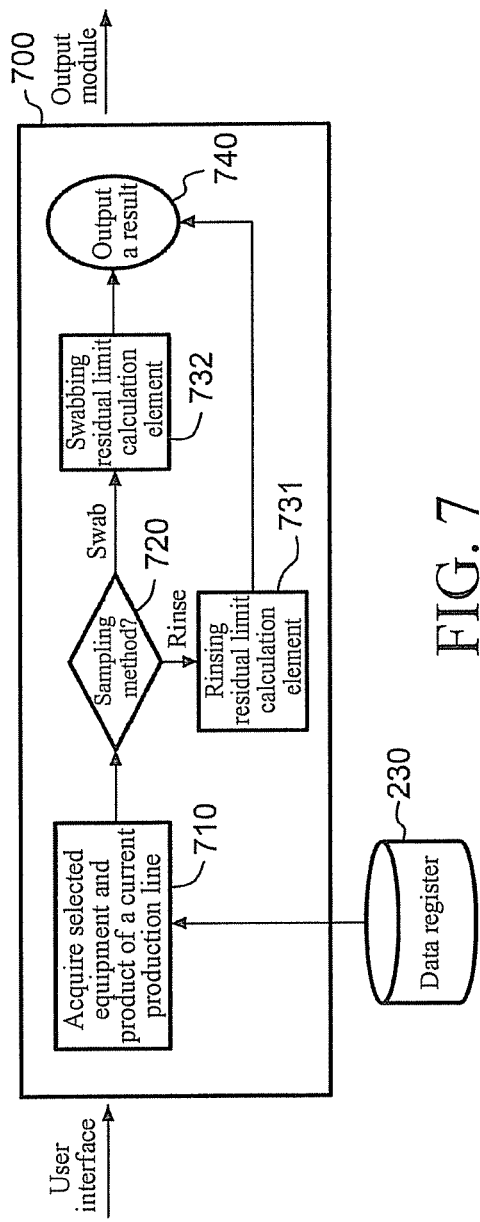
FIG. 7 is a flow chart of a cleaning validation analysis calculation procedure performed by a calculation module according to a specific embodiment.

FIG. 7 is a flow chart of a cleaning validation analysis calculation procedure 700 performed by the calculation module 250 according to a specific embodiment. First, the data register 230 is accessed to acquire data of selected equipment and pharmaceutical of a current production line (Step 710). Next, a sampling method of the selected production line, for example, a rinsing method or a swabbing method, is determined (Step 720). Next, a corresponding product residual limit calculation is performed on the accessed data according to the determined sampling method, for example, the calculation is based on a default product residual limit calculation formula for the rinsing method (Step 731), or on a default product residual limit calculation formula for the swabbing method (Step 732). Finally, the calculation result is provided to the output module 260 (Step 740). A variety of different conventional formulas for product residual limit calculation can be employed, and will not be further illustrated or limited herein.

Figure 8:
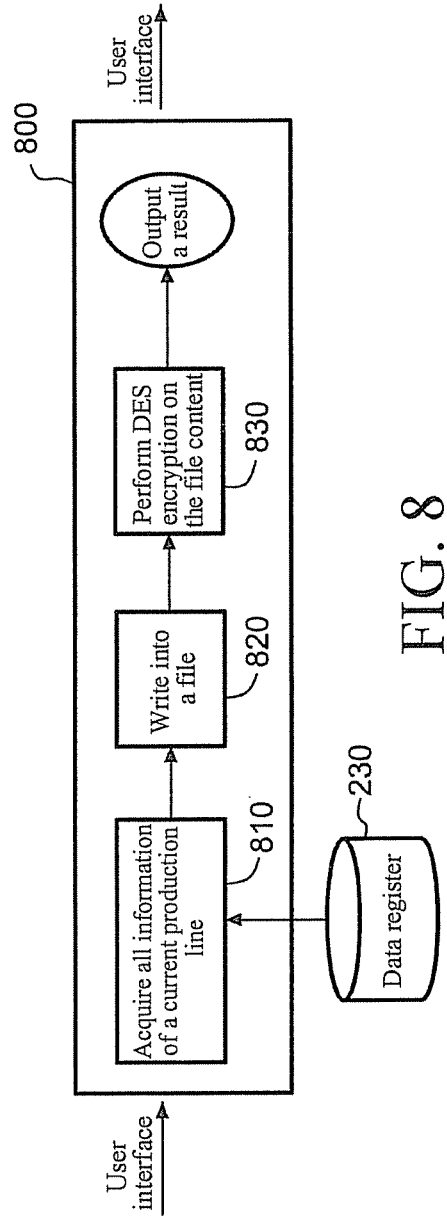
FIG. 8 is a flow chart of a backup operation process of a backup module according to a specific embodiment.

FIG. 8 is a flow chart of a backup operation process 800 of the backup module 240 according to a specific embodiment. First, the data register 230 is accessed to acquire a part of or all the equipment and pharmaceutical information associated with a current production line (Step 810). Next, the acquired information is written into a file (Step 820) which is, for example, in the CSV format, and then the file is encrypted to obtain a backup file (Step 830) which is, for example, in the DES format (an encrypted file format), thereby ensuring that data of the backup file will not be arbitrarily modified. Finally, the backup file is provided via the user interface 270. As described in the explanation about FIG. 2, the backup file can be selected as the input file when the user logs in next time.

As shown in FIG. 2, in view of the above, it is clear that the calculation module 250 can execute the built-in cleaning validation analysis calculation program, thereby automatically completing the recognition of a file attribute, capturing of data fields, and application of calculation formulas. The user can acquire a complete report generated by the system simply by inputting correct data without having to set any calculation formula.

After the above data processing is performed, a calculation result output process may be performed, which is mainly implemented by the output module 260. The output module 260 is configured to summarize the results calculated and analyzed by the calculation module 250, acquire glossary explanation applicable to the type of the selected production line from the database 180, integrate the result and the glossary explanation into a report file, and finally provide the report file via the user interface 270. Therefore, the report file can provide relevant information such as minimum allowable residual quantity values between a plurality of pharmaceuticals on the selected production line, an index pharmaceutical, a suggested production schedule, and a glossary explanation to the user.

Figure 9:
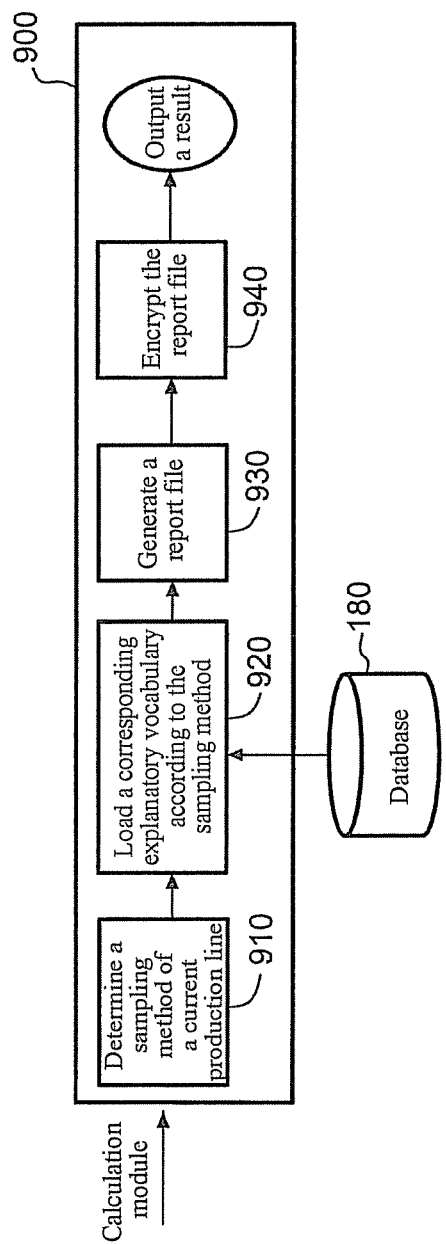
FIG. 9 is a flow chart of an output operation process of an output module according to a specific embodiment.

FIG. 9 is a flow chart of an output operation process 900 of the output module 260 according to a specific embodiment. First, a sampling method of a selected production line is determined (Step 910). Next, an explanatory glossary corresponding to the sampling method is imported from the database 180 according to the determined sampling method (Step 920). Next, a report file is generated according to a calculation and analysis result received by the calculation module 250 and the imported explanatory vocabulary (Step 930). Next, optionally, the report file is encrypted (Step 940). Finally, the report file is provided via the user interface 270 (Step 950).

Pharmaceutical Stability Test Analysis System

To ensure the quality of the pharmaceutical covered by a relevant application, a stability test must be performed to estimate an effective period, i.e., the so-called shelf life, of the pharmaceutical. In particular, the stability test aims to study the relation between pharmaceutical quality and time under the influence of environmental factors such as temperature, humidity, and light, and work out a degradation curve of the pharmaceutical, thereby estimating the shelf-life of the pharmaceutical and ensuring efficacy and safety in use of the pharmaceutical. Regarding details of the stability test, reference can be made to, for example, the Guidelines for Pharmaceutical Stability Testing published by the International Conference on Harmonization of Technical Requirements for Registration of Pharmaceutical for Human Use (ICH) and the Department of Health, Executive Yuan, Taiwan.

One of the applications of the pharmaceutical stability test analysis system 130 in FIG. 1 is to calculate the shelf life of a pharmaceutical. The calculation result can be provided to a user (for example, a pharmaceutical factory worker), so that the user can obtain the shelf-life of the pharmaceutical without designing complex calculation by himself/herself, thereby ensuring the efficacy and safety in use of the pharmaceutical.

Figure 10:
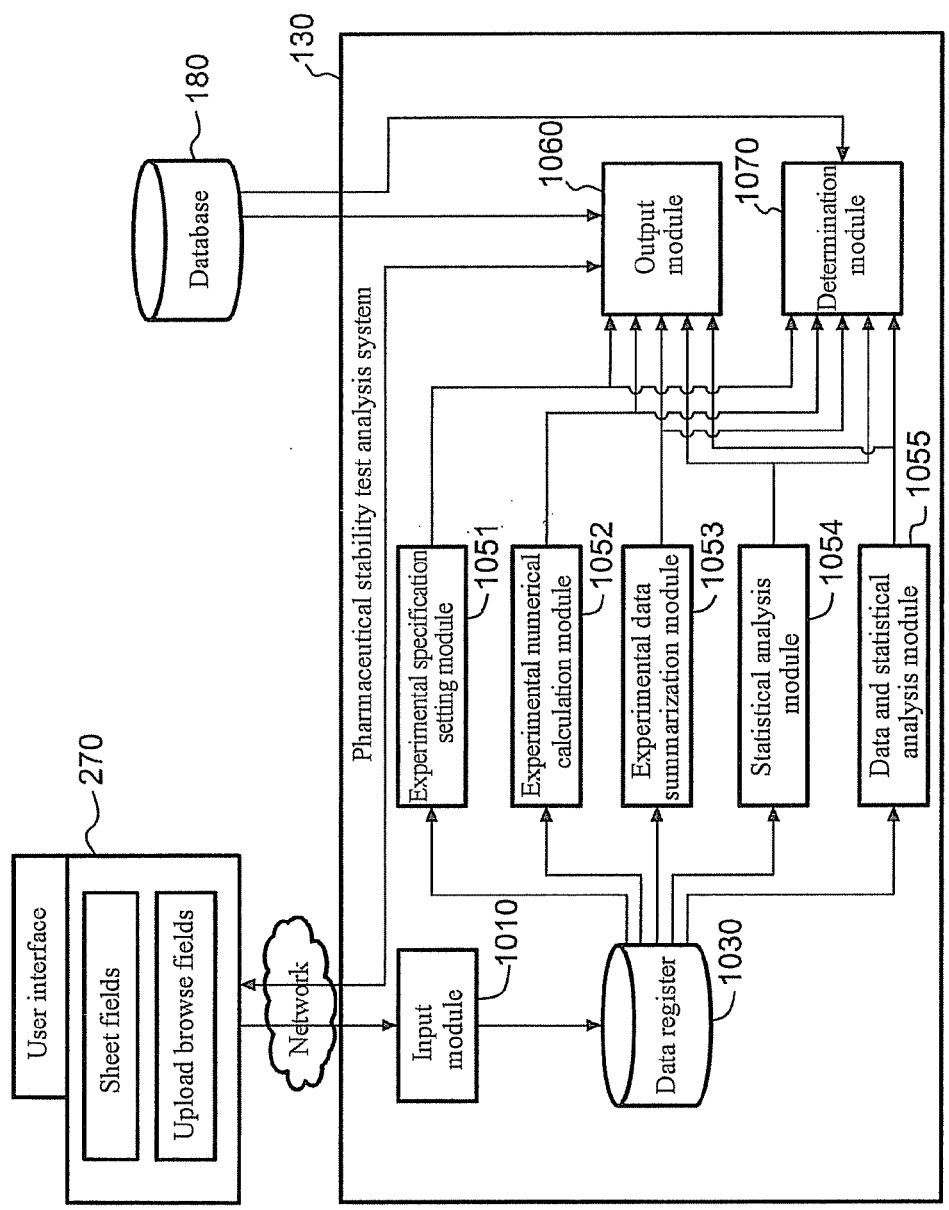
FIG. 10 is a structural view of a pharmaceutical stability test analysis system according to an embodiment.

FIG. 10 is a structural view of the pharmaceutical stability test analysis system 130 according to a specific embodiment. Like the pharmaceutical production cleaning validation system 120 shown in FIG. 2, the pharmaceutical stability test analysis system 130 may include an input module 1010 and an output module 1060 configured to receive data via a user interface 270 and output a calculation result via the user interface 270, respectively. In addition, the pharmaceutical stability test analysis system 130 may also include a data register 1030 and a determination module 1070 for registering and determining, respectively the received data. The form of the data received by the input module 1010 is also at least one input file (which may be a template file or a backup file). The details about the structures and operation processes of the above modules can be deduced from FIG. 2, and will not be described herein again for the sake of conciseness.

However, slightly different from the pharmaceutical production cleaning validation system 120 in FIG. 2, the pharmaceutical stability test analysis system 130 may further include more than one calculation module capable of independent operation. The more than one calculation module may also be shown as different menus on the user interface 270 (for example, an operation screen) for selection by the user.

As shown in FIG. 10, the at least one calculation module may be (or at least one of) an experimental specification setting module 1051, an experimental numerical calculation module 1052, an experimental data summarization module 1053, or a statistical analysis module 1054. These modules are responsible for the complete process of a stability test from specification setting, experimental operation, data calculation, report generation to backup data acquisition. These modules can cooperate with each other to calculate the shelf life of a pharmaceutical step by step according to individual experimental result data in at least one experimental period of a stability test.

In addition, preferably, one of the at least one calculation module may further be a data and statistical analysis module 1055 that can calculate the shelf life of a pharmaceutical according to the complete numerical analysis data in a complete experimental period of a stability test.

It should be noted that the main difference between the data and statistical analysis module 1055 and the entirety of the experimental specification setting module 1051, the experimental numerical calculation module 1052, the experimental data summarization module 1053, and the statistical analysis module 1054 is that, the received numerical analysis data are different, so different numbers of steps need to be performed to estimate the shelf life of a pharmaceutical. In particular, the latter receives individual experimental result data in at least one experimental period, so the complete numerical analysis data in a complete experimental period needed to estimate the shelf life can be acquired only by the statistical analysis module 1054 (i.e., in the last step). However, the data and statistical analysis module 1055 directly receives a complete numerical analysis data in a complete experimental period, and thus can directly estimate the shelf life without step-by-step calculation. Through this configuration, the pharmaceutical stability test analysis system 130 can estimate the shelf life according to different data, thereby meeting different use requirements. It should also be noted that, in another embodiment, the pharmaceutical stability test analysis system 130 can include only the data and statistical analysis module 1055.

In addition, the pharmaceutical stability test analysis system 140 may further include a determination module 1070 configured to authenticate calculation results of the calculation modules and results of conventional software packages (such as SAS) by checking them against each other.

The operation processes of the experimental specification setting module 1051, the experimental numerical calculation module 1052, the experimental data summarization module 1053, and the statistical analysis module 1054 will be explained in detail below.

The experimental specification setting module 1051 is configured to set specification data of a stability test including at least one experimental item. The specification data is basic data required in the stability experiment and may include, for example, at least one of individual experimental type data, individual experimental time data (for example, an experimental starting date and a total number of experimental months), individual storage condition data (for example, temperature and humidity), and individual packaging condition data of the at least one experimental item. The specification data may further include information about a pharmaceutical to be subjected to the stability test, for example, a pharmaceutical name, a pharmaceutical batch number, and a pharmaceutical sampling quantity.

Figure 11:
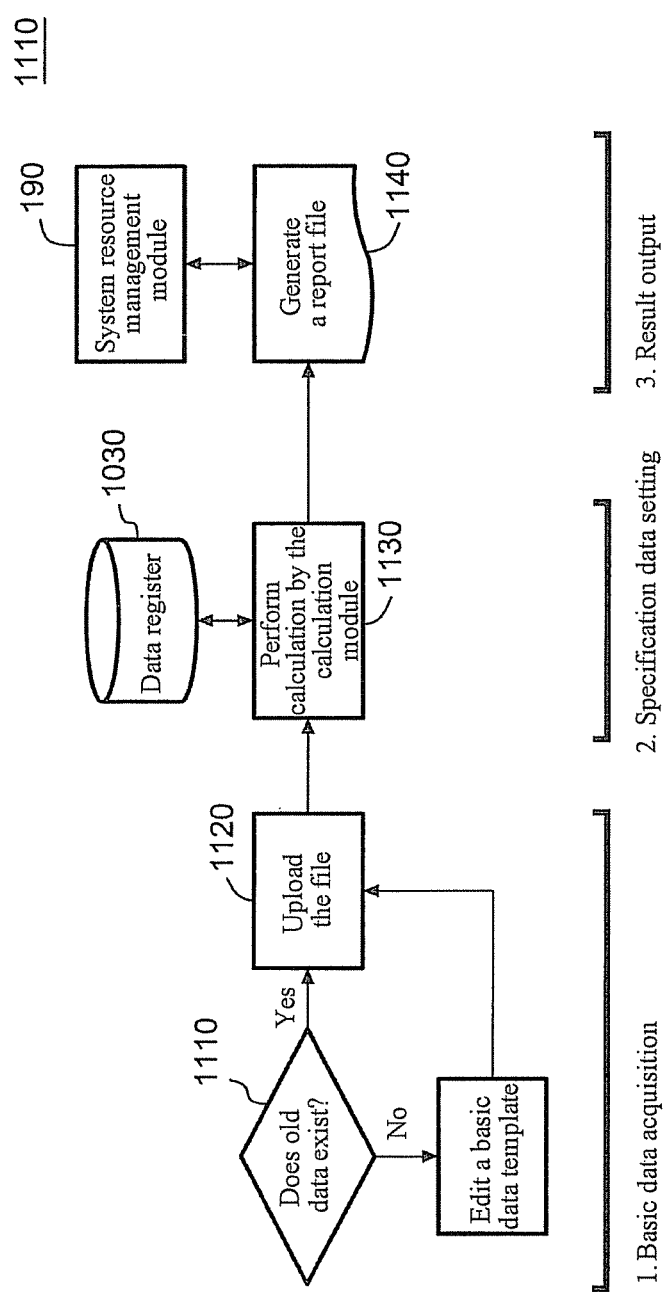
FIG. 11 is a flow chart of an experimental specification setting procedure according to a specific embodiment.

FIG. 11 is a flow chart of an experimental specification setting procedure 1100 according to a specific embodiment. As shown in FIG. 11, first, an input file containing specification data is acquired by: determining whether old data (i.e., a backup file containing specification data) exists (Step 1110), and uploading a specification data template file edited by the user to the input module 1010 if not, or directly uploading the backup file to the input module 1010 (Step 1120) if so.

Next, the specification data is set (Step 1130), in which the experimental specification setting module 1051 performs calculation such as organization and conversion according to the basic data provided by the input file (the specification data template file or the backup file). For example, a corresponding date of each month may be generated according to an experimental starting date and a total number of experimental months, and then a calculation result is provided to the output module 1060.

Finally, the calculation result is output (Step 1140), in which the output module 1060 generates an output report (for example, in a PDF format) according to the above calculation result.

The experimental numerical calculation module 1052 is configured to perform numerical operation using a plurality of different default calculation formulas according to specification data of a stability test of a pharmaceutical and individual experimental result data in at least one experimental period, thereby obtaining individual numerical analysis data of the pharmaceutical in the at least one experimental period. In an embodiment, the individual numerical analysis data in the at least one experimental period may include at least one of standard concentration data, sample concentration data, principal component content data, impurity content data, dissolution data, relative standard deviation value data, uniformity data, and test result data of the pharmaceutical.

Figure 12:
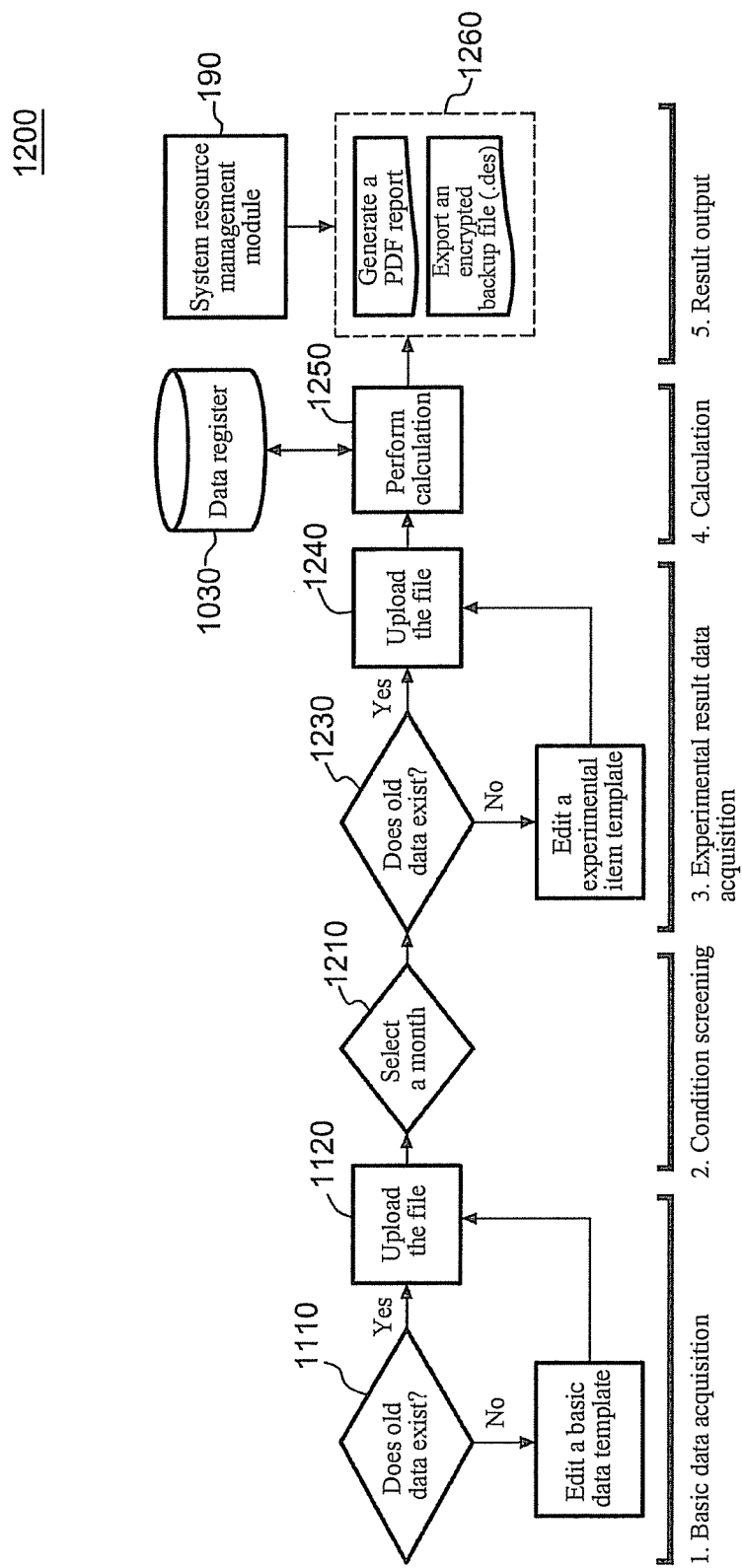
FIG. 12 is a flow chart of an experimental numerical calculation procedure according to a specific embodiment.

FIG. 12 is a flow chart of an experimental numerical calculation procedure 1200 according to a specific embodiment. Similar to the procedure shown in FIG. 11, first, an input file containing specification data is acquired by performing Steps 1110 and 1120. However, if the specification data already exists in the data register, the two steps can be omitted.

Next, condition screening is performed, for example, an experimental period (for example, an experimental month) may be selected (Step 1210). Since the experimental to be performed in different experimental periods are not the same, the user can select an experimental period for calculation according to his/her requirements.

Next, experimental result data corresponding to the experimental month is acquired by performing Steps 1230 and 1240. Steps 1230 and 1240 are similar to Steps 1110 and 1120, respectively, and the only difference is that at least one input file (for example, an experimental item template file or an experimental item backup file) containing experimental result data is acquired here. In an embodiment, the at least one input file is related to different dosage forms of a pharmaceutical, for example, it may be a solid template file or a liquid template file.

Next, data calculation is performed (Step 1250), in which the experimental numerical calculation module 1052 performs numerical calculation according to the specification data and the experimental result data of the two input files obtained in Steps 1120 and 1240, so as to obtain numerical analysis data of the pharmaceutical in the selected experimental period and provide the calculation result to the output module 1060.

Next, the calculation result is output (Step 1260), in which the output module 1060 may generate at least one of a report file (for example, in PDF format) for reading by the user and a backup file (preferably in encrypted DES format) for use by the experimental data summarization module 1053. It should be noted that, Steps 1230 to 1260 may be repeated several times, thereby obtaining calculation results corresponding to different selected experimental periods.

The experimental data summarization module 1053 is configured to obtain by summarization complete numerical analysis data of a pharmaceutical in a complete experimental period (for example, 6 months) of a stability test according to individual numerical analysis data of the pharmaceutical in at least one experimental period (for example, from the first month to the sixth month). The individual numerical analysis data may be provided by the backup file generated in the experimental numerical calculation procedure 1200.

Figure 13:
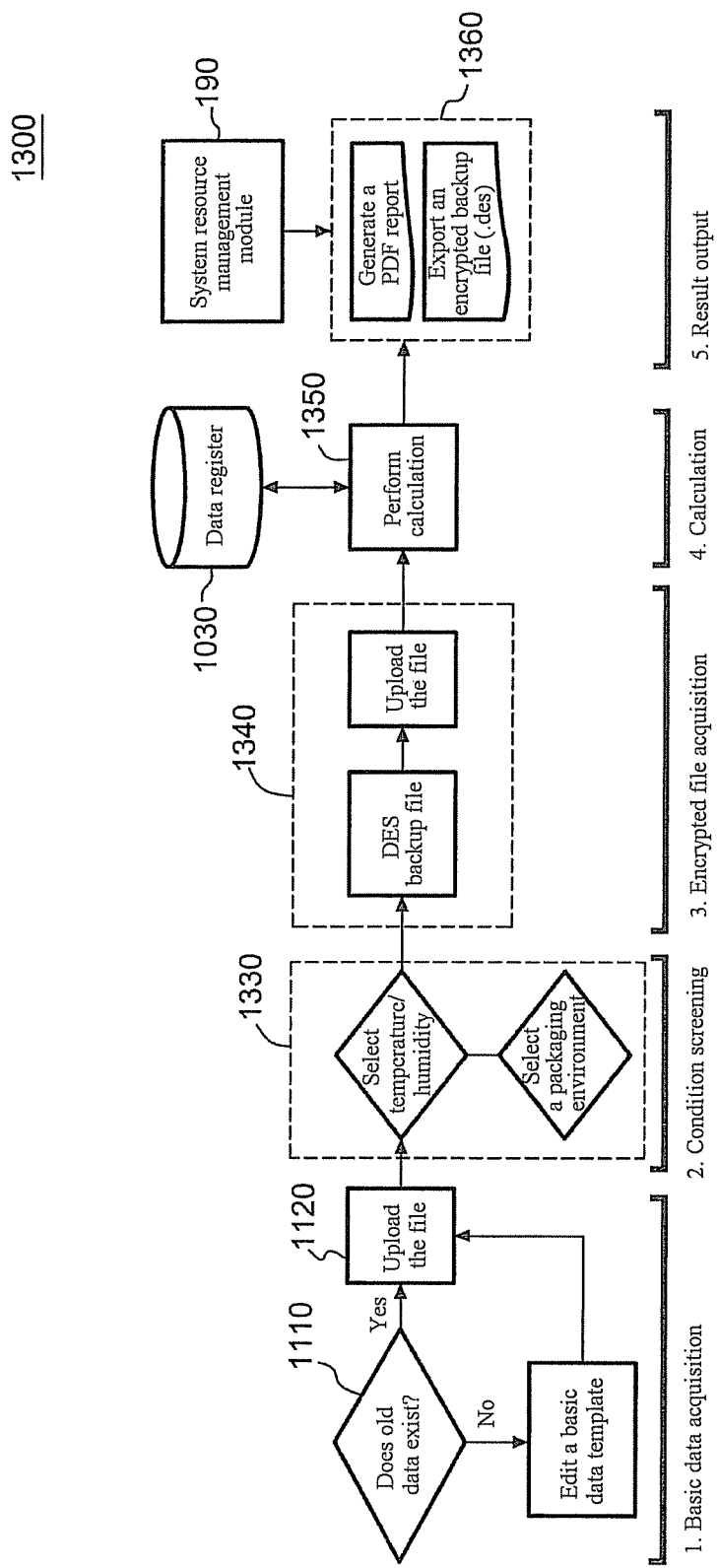
FIG. 13 is a flow chart of an experimental data summarization procedure according to a specific embodiment.

FIG. 13 is a flow chart of an experimental data summarization procedure 1300 according to a specific embodiment. Similar to the procedure shown in FIG. 12, first, an input file containing specification data is acquired by performing Steps 1110 and 1120. However, if the specification data already exists in the data register, the two steps may be omitted.

Next, condition screening is performed (Step 1330), for example, a storage condition (temperature and humidity) and a packaging condition may be selected.

Next, individual numerical analysis data in at least one experimental period is acquired (Step 1340). For example, the input module 1010 may obtain at least one backup file corresponding to the at least one experimental period, which may be the backup file generated in the experimental numerical calculation procedure 1200.

Next, the individual numerical analysis data of the at least one experimental period is summarized (Step 1350), in which the experimental data summarization module 1053 summarizes the specification data and the numerical analysis data obtained in Steps 1120 and 1340, so as to obtain numerical analysis data (referred to as complete numerical analysis data) of a pharmaceutical in a complete experimental period (formed by the at least one experimental period) and provide a calculation result to the output module 1060. This process may involve conversion of the experimental period, for example, a corresponding date of each month is generated according to an experimental starting date and a total number of experimental months.

Next, the calculation result is output (Step 1360), in which the output module 1060 may generate at least one of a report file (for example, in PDF format) for reading by the user and a backup file (preferably in encrypted DES format) for use by the statistical analysis module 1054.

The statistical analysis module 1054 is configured to calculate the shelf life of the pharmaceutical according to the complete numerical analysis data (including relevant data for calculating the shelf life) in a complete experimental period of a stability test. The above complete numerical analysis data may be provided by the backup file generated in the experimental data summarization procedure 1300.

Figure 14:
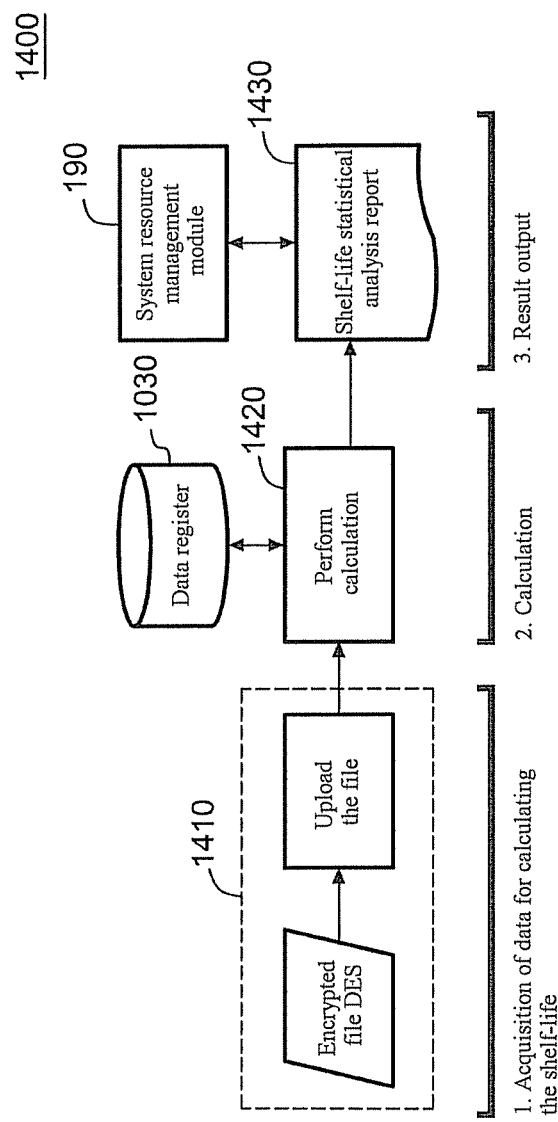
FIG. 14 is a flow chart of a statistical analysis procedure according to a specific embodiment.

FIG. 14 is a flow chart of a statistical analysis procedure 1400 according to a specific embodiment. Similar to the procedure shown in FIG. 13, first, an input file containing the complete numerical analysis data in a complete experimental period is acquired (Step 1410). For example, the input module 1010 may obtain a backup file having relevant data for calculating a shelf life which may be the backup file generated in the experimental data summarization procedure 1300.

Next, the statistical analysis module 1054 calculates the shelf life of the pharmaceutical using a given formula according to the received complete numerical analysis data, and provides a calculation result to the output module 1060 (Step 1420). A variety of different conventional calculation formulas can be employed, and will not be further illustrated or limited herein.

Next, the calculation result is output (Step 1430), in which the output module 1060 may generate a report file (for example, in PDF format) with statistical analysis of the shelf life for reading by the user.

The data and statistical analysis module 1055 is configured to calculate the shelf life of the pharmaceutical according to the complete numerical analysis data in a complete experimental period of a stability test. It should be noted that the main difference between the data and statistical analysis module 1055 and the statistical analysis module 1054 is that the complete numerical analysis data on which the former is based may be obtained from a shelf-life template file edited by the user, while the complete numerical analysis data on which the latter is based may be obtained from the backup file generated in the statistical analysis procedure 1400.

Figure 15:
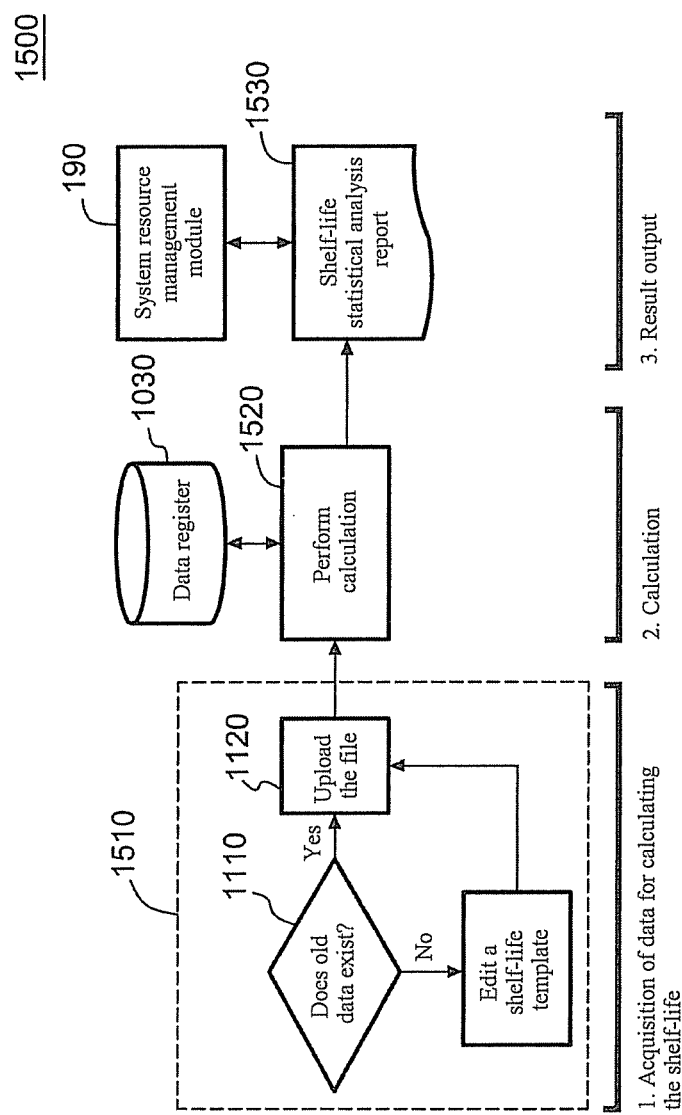
FIG. 15 is a flow chart of a data and statistical analysis procedure according to a specific embodiment.

FIG. 15 is a flow chart of a data and statistical analysis procedure 1500 according to a specific embodiment. First, an input file containing the complete numerical analysis data in a complete experimental period is acquired (Step 1510). For example, the input module 1010 may obtain an input file having relevant data for calculating a shelf life which may be a shelf-life template file edited by the user or a previously output backup file.

Next, the data and statistical analysis module 1055 calculates the shelf life of the pharmaceutical using a given formula according to the received complete numerical analysis data, and provides a calculation result to the output module 1060 (Step 1520). As illustrated in Step 1420, a variety of different conventional calculation formulas can be employed, and will not be further illustrated or limited herein.

Next, the calculation result is output (Step 1530), in which the output module 1060 may generate a report file (for example, in PDF format) with statistical analysis of the shelf-life for reading by the user.

Pharmaceutical Analysis Method Validation System

Before it can register a pharmaceutical, a pharmaceutical factory is responsible for validating an analysis method of the pharmaceutical to determine whether the analysis method can really applied to achieve the intended purposes. In other words, the validation of the analysis method may be explained as a procedure established by the laboratory after research, which displays the features of an analysis method when the analysis method meets the requirements of a desired analysis. For details of the analysis method validation, reference can be made to the Current Good Pharmaceutical Manufacturing Practices—Analytical Method Validation Guidelines published by the Department of Health, Executive Yuan, Taiwan.

One of the applications of the pharmaceutical analysis method validation system 140 in FIG. 1 is to effectively calculate analytical representative characteristics such as specificity, linearity and range, accuracy, precision, minimum detectable concentration, and minimum quantitative concentration according to different analysis methods in selected different test items. The calculation results may be provided to a user (for example, a pharmaceutical factory worker) as a reference to determine whether the above analysis methods achieve the intended purposes.

Figure 16:
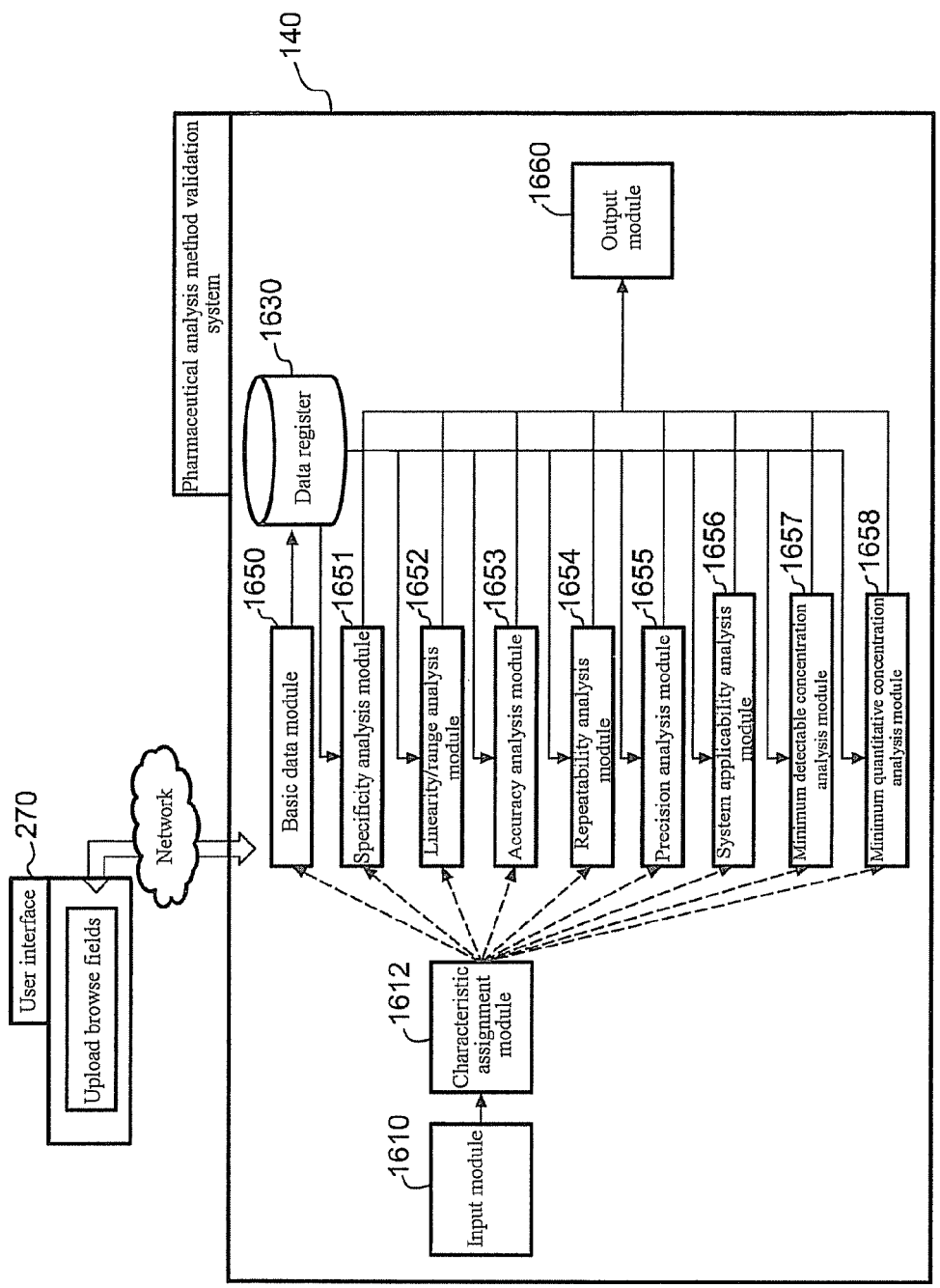
FIG. 16 is a structural view of a pharmaceutical analysis method validation system according to an embodiment.

FIG. 16 is a structural view of the pharmaceutical analysis method validation system 140 according to an embodiment. The pharmaceutical analysis method validation system 140 is configured to obtain the analysis data of at least one characteristic of a pharmaceutical according to experimental result data of the pharmaceutical. Like the pharmaceutical production cleaning validation system 120 shown in FIG. 2, the pharmaceutical analysis method validation system 140 may include an input module 1610 and an output module 1660 configured to receive data via a user interface 270 and output a calculation result via the user interface 270, respectively. In addition, the pharmaceutical analysis method validation system 140 may also include at least one of a data register 1630 and a backup module (not shown) for registering and backing up the received data, respectively.

In addition, the form of the data received by the input module 1610 is also at least one input file (which may be a template file). Details about the structures and operation processes of the above modules can be deduced from FIG. 2, and will not be described herein again for the sake of conciseness.

However, slightly different from the pharmaceutical production cleaning validation system 120 in FIG. 2, the pharmaceutical analysis method validation system 140 may include more than one calculation module which may be at least one of the following characteristic analysis modules: a specificity analysis module 1651, a linearity/range analysis module 1652, an accuracy analysis module 1653, a repeatability analysis module 1654, a precision analysis module 1655, a system applicability analysis module 1656, a minimum detectable concentration analysis module 1657, and a minimum quantitative concentration analysis module 1658.

In a preferred embodiment, the characteristic analysis modules 1651-1658 perform calculation according to the data in their respective template files. In particular, after the input module 1610 receives different template files, the characteristic analysis modules 1651-1658 may then execute a built-in corresponding characteristic analysis program, so as to perform a corresponding analytical characteristic item calculation on the pharmaceutical using respective default formulas according to the data in the respective template files. A variety of different conventional default formulas for characteristic analysis can be employed, and will not be further illustrated or limited herein.

In addition, the pharmaceutical analysis method validation system 140 may further include a basic data module 1650 and a characteristic assignment module 1612. Since the templates received by the input module 1610 have different content formats due to association with different analytical characteristics, and the type and number of input files chosen to be uploaded by the user are random, it is necessary to recognize the received input files to assign them to the corresponding characteristic analysis modules.

In an embodiment, the input module 1610 may receive a basic data input file (which may be a template file or modified from a template file) containing basic data and at least one characteristic analysis input file (which may be a template file or a backup file) containing different characteristic analysis data. The basic data includes analysis item data for designating at least one characteristic analysis item to be performed.

The basic data module 1650 can then read the basic data and obtain the at least one characteristic analysis item. The characteristic assignment module 1612 can identify an attribute of the at least one characteristic analysis input file, so as to assign the data of the at least one characteristic analysis input file to corresponding ones of the at least one characteristic analysis module 1651-1658 according to the identified attribute.

Figure 17:
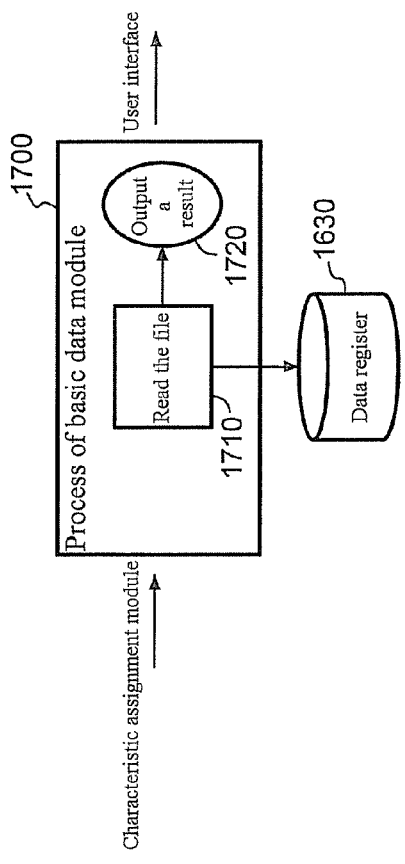
FIG. 17 is a flow chart of an operation process of a basic data module according to an embodiment.

FIG. 17 is a flow chart of an operation process 1700 of the basic data module 1650 according to an embodiment. As shown in FIG. 17, the basic data module 1650 simply reads the content of the basic data input file and stores the basic data in the data register 1630 (Step 1710), and then the user interface 270 can show the read result (Step 1720).

Figure 18:
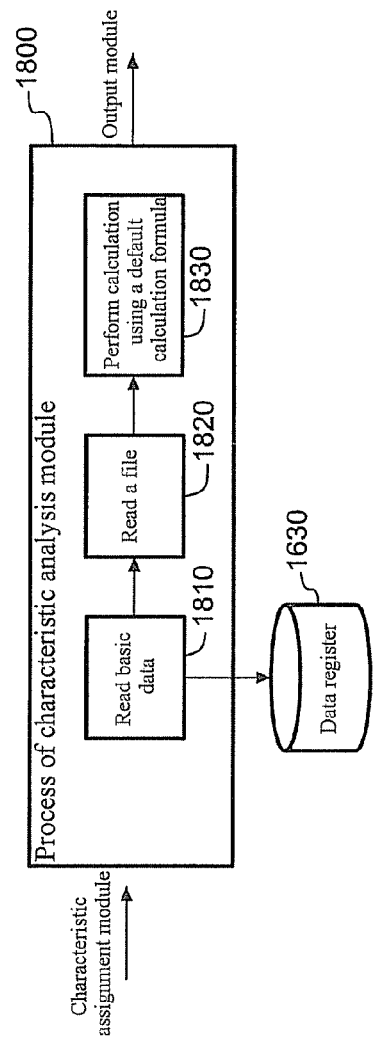
FIG. 18 is a flow chart of an operation process of any one of the characteristic analysis modules according to an embodiment.

FIG. 18 is a flow chart of an operation process of any one of the characteristic analysis modules 1651-1658 according to an embodiment. As shown in FIG. 18, first, basic data is read from the data register 1630 (Step 1810), then a characteristic analysis input file is read (Step 1820), and then calculation is performed using a default analysis calculation formula, and a calculation result is provided to the output module 1660 (Step 1830). It should be noted that the output module 1660 may further integrate the results output by different characteristic analysis modules, so as to output a single report file. For any one of the characteristic analysis modules 1651-1658, a variety of different conventional analysis calculation formulas can be employed, and will not be further illustrated or limited herein.

It should be noted that, in the above embodiments, the respective input module, output module, backup module, and data register are depicted in drawings and illustrated for each pharmaceutical manufacturing and research and development numerical analysis system. However, in interpretation of the drawings or illustration, persons of ordinary skill in the art should know that the specific input modules, output modules, backup modules, and data registers of the pharmaceutical manufacturing and research and development numerical analysis systems may be the same or different input modules, output modules, backup modules, and data registers.

It should be noted that the present invention may also be implemented by a computer readable recording medium. In an embodiment, the computer readable recording medium may be a storage medium such as an optical disk, a hard disk, a tape, or a memory. The computer readable recording medium may store raw experimental data and analysis results, in which the instructions are configured to execute an integrated pharmaceutical manufacturing and research and development numerical analysis method (including corresponding steps in operation processes of the components in the server for integrated pharmaceutical analysis and report generation service 100), so as to be provided to a computing device capable of executing the instructions.

The differences between the server for integrated pharmaceutical analysis and report generation service 100 and the conventional pharmaceutical manufacturing and research and development numerical analysis calculation techniques and the main advantages of the server 100 will be summarized below.

First Advantage: Simple Operation

The interaction between a user and the server for integrated pharmaceutical analysis and report generation service 100 is mainly achieved via a user interface (for example, a webpage interface). To acquire a calculated report result via the user interface, the user only needs to input and store relevant data under the guide of input items in a template file, and then select an input file to be calculated via the user interface for upload.

Such an operation mode is entirely different from that of conventional software packages. As described above, in the conventional software packages, the use interface function is divided and hidden in different sub-window functional menus, or special program instructions need to be used in order to display an interface for input by the user, and the user further needs special program syntax in order to accomplish the data calculation and report generation. In contrast, a user of the server for integrated pharmaceutical analysis and report generation service 100 only needs the user to fill in complete and correct raw data.

Second Advantage: Fast Calculation

As described above, in numerical calculation of the conventional software packages, filling in different numerical values or manual selection of a calculation mode is required in each step, as a result, complete calculation takes a lot of time, and the user often needs to integrate calculation results of different software packages in order to complete a part of calculation work.

In contrast, the server for integrated pharmaceutical analysis and report generation service 100 does not have such a complex process. The user only needs to select and determine an input file to be uploaded without assigning or setting any calculation mode or procedure. After receiving the input file uploaded by the user, the system may look for a corresponding algorithm according to an attribute of the file. Even when an exceptional calculation method is designed according to requirements, the server for integrated pharmaceutical analysis and report generation service 100 can provide simple identification, thereby avoiding causing too much trouble to the user.

Third Advantage: High Accuracy

Different from the conventional manual calculation formula setting and field capturing in EXCEL®, in the server for integrated pharmaceutical analysis and report generation service 100, both calculation formula setting and field capturing are automatically done by the system without user intervention, so human errors are greatly reduced, thereby increasing the reliability of calculation results.

In accordance with an example embodiment, a computing device can be configured to perform one or more functions of one or more modules and/or systems described herein, including, but not limited to, pharmaceutical manufacturing and research and development numerical analysis system 120. The computing device can include a user interface module, a network-communication interface module, one or more processors, and data storage, all of which can be linked together via a system bus, network, or other connection mechanism.

The user interface module can be operable to send data to and/or receive data from external user input/output devices. For example, the user interface module can be configured to send/receive data to/from user input devices such as a keyboard, a keypad, a touch screen, a computer mouse, a track ball, a joystick, and/or other similar devices, now known or later developed. The user interface module can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module can also be configured to generate audible output(s), such as a speaker, speaker jack, audio output port, audio output device, earphones, and/or other similar devices, now known or later developed.

The network-communications interface module can include one or more wireless interfaces and/or wireline interfaces that are configurable to communicate via a network, such as the network 106 shown in FIG. 1. The wireless interfaces can include one or more wireless transceivers, such as a Bluetooth transceiver, a Wi-Fi transceiver perhaps operating in accordance with an IEEE 802.11 standard (e.g., 802.11a, 802.11b, 802.11g), a WiMAX transceiver perhaps operating in accordance with an IEEE 802.16 standard, and/or other types of wireless transceivers configurable to communicate via a wireless network. The wireline interfaces can include one or more wireline transceivers, such as an Ethernet transceiver, a Universal Serial Bus (USB) transceiver, or similar transceiver configurable to communicate via a wire, a twisted pair of wires, a coaxial cable, an optical link, a fiber-optic link, or other physical connection to a wireline network.

In some embodiments, the network communications interface module can be configured to provide reliable, secured, compressed, and/or authenticated communications. For each communication described herein, information for ensuring reliable communications (e.g., guaranteed message delivery) can be provided, perhaps as part of a message header and/or footer (e.g., packet/message sequencing information, encapsulation header(s) and/or footer(s), size/time information, and transmission verification information such as cyclic redundancy check (CRC) and/or parity check values). Communications can be compressed and decompressed using one or more compression and/or decompression algorithms and/or protocols such as, but not limited to, one or more lossless data compression algorithms and/or one or more lossy data compression algorithms. Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

The one or more processors can include one or more general purpose processors and/or one or more special purpose processors (e.g., digital signal processors, application specific integrated circuits, etc.). The one or more processors can be configured to execute computer-readable program instructions that are contained in the data storage and/or other instructions as described herein.

The data storage can include one or more computer-readable storage media that can be read or accessed by at least one of the processors. The one or more computer-readable storage media can include volatile and/or non-volatile storage components, such as optical, magnetic, organic or other memory or disc storage, which can be integrated in whole or in part with at least one of the one or more processors. In some embodiments, the data storage can be implemented using a single physical device (e.g., one optical, magnetic, organic or other memory or disc storage unit), while in other embodiments, the data storage can be implemented using two or more physical devices.

Computer-readable storage media associated with data storage and/or other computer-readable media described herein can also include non-transitory computer-readable media such as computer-readable media that stores data for short periods of time like register memory, processor cache, and random access memory (RAM). Computer-readable storage media associated with data storage and/or other computer-readable media described herein can also include non-transitory computer readable media that stores program code and/or data for longer periods of time, such as secondary or persistent long term storage, like read only memory (ROM), optical or magnetic disks, compact-disc read only memory (CD-ROM), for example. Computer-readable storage media associated with data storage and/or other computer-readable media described herein can also be any other volatile or non-volatile storage systems. Computer-readable storage media associated with data storage and/or other computer-readable media described herein can be considered computer readable storage media for example, or a tangible storage device.

The data storage can include computer-readable program instructions and perhaps additional data. In some embodiments, the data storage can additionally include storage required to perform at least part of the herein-described techniques, procedures, processes, methods, and/or at least part of the functionality of the herein-described devices and networks.

The present invention has been disclosed through preferred embodiments, but is not intended to be limited thereto. Various variations and modifications made by persons skilled in the art without departing from the spirit and scope of the present invention fall within the scope of the present invention as defined by the appended claims.

We claim:

1. A server for integrated pharmaceutical analysis and report generation service, comprising:
    at least one pharmaceutical manufacturing and research and development numerical analysis system, configured to perform different pharmaceutical manufacturing and research and development numerical analyses, wherein each of the at least one pharmaceutical manufacturing and research and development numerical analysis system comprises:
    an input module configured to receive, via a user interface, a first backup file previously generated by the pharmaceutical manufacturing and research and development numerical analysis system as at least one input file, wherein the at least one input file comprises a plurality of data fields to provide corresponding data, wherein no calculation mode or procedure is set or assigned via the user interface, and wherein the data fields of the at least one input file comprise at least one of production line information, equipment information, and pharmaceutical information;
    at least one calculation module configured to execute a built-in pharmaceutical manufacturing and research and development numerical analysis calculation program corresponding to at least one of the plurality of data fields of the at least one input file, thereby automatically performing a pharmaceutical manufacturing and research and development numerical analysis calculation on at least one of the data of the at least one input file and data entered online; and
    an output module configured to generate a second backup file as at least one output file based on a result of the pharmaceutical manufacturing and research and development numerical analysis performed by the at least one calculation module, and provide the at least one output file via the user interface.

2. The server for integrated pharmaceutical analysis and report generation service according to claim 1, wherein the server for integrated pharmaceutical analysis and report generation service is a network server located at a server side, and the user interface is a web page interface located at a client.

3. The server for integrated pharmaceutical analysis and report generation service according to claim 1, further comprising a data register for registering data associated with a user when the user logs in and removing the data associated with the user when the user logs out.

4. The server integrated pharmaceutical analysis and report generation service according to claim 3, further comprising a backup module for backing up at least a part of data in the data register as the first backup file and providing the first backup file via the user interface.

5. The server for integrated pharmaceutical analysis and report generation service according to claim 1, wherein the at least one pharmaceutical manufacturing and research and development numerical analysis system comprises a pharmaceutical production line cleaning validation system comprising the at least one calculation module, the pharmaceutical manufacturing and research and development numerical analysis calculation performed by the at least one calculation module in the pharmaceutical production line cleaning validation system comprises performing at least one of the following procedures on a plurality of pharmaceuticals on each of at least one production line:
    calculating minimum allowable residual quantity values between the pharmaceuticals;
    screening an index pharmaceutical from the pharmaceuticals; and
    analyzing a suggested production schedule of the pharmaceuticals.

6. The server for integrated pharmaceutical analysis and report generation service according to claim 5, wherein the pharmaceutical production line cleaning validation system further comprises a management module configured to perform at least one of production line information management, equipment information management, and pharmaceutical information management.

7. The server for integrated pharmaceutical analysis and report generation service according to claim 1, wherein the at least one pharmaceutical manufacturing and research and development numerical analysis system comprises a pharmaceutical stability test analysis system configured to analyze and calculate a shelf-life of pharmaceuticals, the pharmaceutical stability test analysis system comprising the at least one calculation module.

8. The server for integrated pharmaceutical analysis and report generation service according to claim 7, wherein the at least one calculation module in the pharmaceutical stability test analysis system comprises at least one of the following modules:
    an experimental specification setting module, configured to set a specification data of a stability test of the pharmaceuticals, wherein the stability test comprises at least one test of an experimental item;
    an experimental numerical calculation module, configured to determine, based on the specification data of the stability test of the pharmaceuticals and individual experimental result data in at least one experimental period, individual numerical analysis data of the pharmaceuticals in the at least one experimental period;
    an experimental data summarization module, configured to determine complete numerical analysis data of the pharmaceuticals in a complete experimental period of the stability test according to the individual numerical analysis data of the pharmaceuticals in at least one experimental period; and
    a statistical analysis module, configured to calculate the shelf life of the pharmaceuticals according to the complete numerical analysis data in the complete experimental period of the stability test.

9. The server for integrated pharmaceutical analysis and report generation service according to claim 8, wherein
    the experimental data summarization module outputs the complete numerical analysis data to the output module;
    the output module generates at least one of the second backup file and a report file according to the complete numerical analysis data; and the input module receives the second backup file as the input file to provide the statistical analysis module when a user logs in another time.

10. The server for integrated pharmaceutical analysis and report generation service according to claim 7, wherein
the at least one calculation module in the pharmaceutical stability test analysis system is a data and statistical analysis module configured to calculate the shelf-life of the pharmaceutical according to the complete numerical analysis data in the complete experimental period of a stability test; and
the input module receives the input file via the user interface, and the input file has the complete numerical analysis data and is provided to the data and statistical analysis module as the input file.

11. The server for integrated pharmaceutical analysis and report generation service according to claim 8, wherein the specification data comprises: at least one of individual experimental type data, individual experimental time data, individual storage condition data, and individual packaging condition data of the at least one experimental item.

12. The server for integrated pharmaceutical analysis and report generation service according to claim 8, wherein the complete numerical analysis data of the pharmaceutical in the complete experimental period is associated with at least one of a selected storage condition and a selected packaging condition.

13. The server for integrated pharmaceutical analysis and report generation service according to claim 8, wherein the individual numerical analysis data in the at least one experimental period comprises at least one of standard concentration data, sample concentration data, principal component content data, impurity content data, dissolution data, relative standard deviation value data, uniformity data, and test result data of the pharmaceuticals.

14. The server for integrated pharmaceutical analysis and report generation service according to claim 1, wherein the at least one pharmaceutical manufacturing and research and development numerical analysis system comprises a pharmaceutical analysis method validation system configured to obtain at least one characteristic analysis data of a pharmaceutical according to experimental result data of the pharmaceutical, the pharmaceutical analysis method validation system comprising the at least one calculation module.

15. The server for integrated pharmaceutical analysis and report generation service according to claim 14, wherein the at least one calculation module in the pharmaceutical analysis method validation system comprises at least one of the following characteristic analysis modules: a specificity analysis module, a linearity/range analysis module, an accuracy analysis module, a repeatability analysis module, a precision analysis module, a system applicability analysis module, a minimum detectable concentration analysis module, and a minimum quantitative concentration analysis module.

16. The server for integrated pharmaceutical analysis and report generation service according to claim 15, wherein the pharmaceutical analysis method validation system further comprises:
a basic data module, configured to read at least one of an input file containing analysis item data and on-line filled data, wherein the analysis item data is used to designate at least one characteristic analysis item to be performed; and
a characteristic assignment module, configured to identify an attribute of the at least one input file received by the input module, wherein the at least one input file is respectively associated with the at least one characteristic analysis item, and assigned to the corresponding one of the at least one characteristic analysis module according to the identified attribute of the at least one input file.

17. The server for integrated pharmaceutical analysis and report generation service according to claim 1, wherein the input module is configured to receive, via the user interface, a template file as the at least one input file, and wherein the output module is configured to generate a report file as the at least one output file.

18. A method of integrated pharmaceutical manufacturing and research and development numerical analysis, comprising:
performing at least one pharmaceutical manufacturing and research and development numerical analysis procedure, wherein each of the at least one pharmaceutical manufacturing and research and development numerical analysis procedure comprises:
receiving, via a user interface, a first backup file previously output by the pharmaceutical manufacturing and research and development numerical analysis procedure as at least one input file, wherein the at least one input file comprises a plurality of data fields to provide corresponding data, wherein no calculation mode or procedure is set or assigned via the user interface, and wherein the data fields of the at least one input file contain at least one of production line information, equipment information, and pharmaceutical information;
executing a built-in pharmaceutical manufacturing and research and development numerical analysis calculation program corresponding to at least one of the plurality of data fields of the at least one input file, thereby automatically performing a pharmaceutical manufacturing and research and development numerical analysis calculation on at least one of the data of the at least one input file and data entered online; and
generating a second backup file as at least one output file based on a result of the pharmaceutical manufacturing and research and development numerical analysis calculation, and providing the at least one output file via the user interface.

19. The method of integrated pharmaceutical manufacturing and research and development numerical analysis according to claim 18, wherein the method of integrated pharmaceutical manufacturing and research and development numerical analysis is implemented at a server side, and the user interface is a webpage interface located at a client.

20. The method of integrated pharmaceutical manufacturing and research and development numerical analysis according to claim 18, further comprising registering data associated with a user when the user logs in and removing the data associated with the user when the user logs out.

21. The method of integrated pharmaceutical manufacturing and research and development numerical analysis according to claim 18, further comprising backing up at least a part of data in the data associated with the user as the first backup file and providing the first backup file via the user interface.

22. The method of integrated pharmaceutical manufacturing and research and development numerical analysis according to claim 18, wherein the at least one pharmaceutical manufacturing and research and development numerical analysis procedure is a cleaning validation procedure, and the cleaning validation procedure comprises performing at least one of the following steps on a plurality of pharmaceuticals on each of at least one production line:
calculating minimum allowable residual quantity values between the pharmaceuticals;

screening an index pharmaceutical from the pharmaceuticals; and analyzing a suggested production schedule of the pharmaceuticals.

23. The method of integrated pharmaceutical manufacturing and research and development numerical analysis according to claim 22, wherein the data fields of the at least one input file contain at least one of production line information, equipment information, and pharmaceutical information.

24. The method of integrated pharmaceutical manufacturing and research and development numerical analysis according to claim 18, wherein the at least one pharmaceutical manufacturing and research and development numerical analysis calculation is a stability test analysis procedure for analyzing and calculating a shelf-life of the pharmaceuticals.

25. The method of integrated pharmaceutical manufacturing and research and development numerical analysis according to claim 24, wherein the stability test analysis procedure comprises at least one of the following steps:
   setting a specification data of the stability test of the pharmaceuticals, wherein the stability test comprises at least one experimental item;
   performing numerical operation according to the specification data of the stability test of the pharmaceuticals and individual experimental result data in at least one experimental period, thereby obtaining individual numerical analysis data of the pharmaceuticals in the at least one experimental period;
   obtaining by summarization the complete numerical analysis data of the pharmaceuticals in a complete experimental period of the stability test according to individual numerical analysis data of the pharmaceutical in at least one experimental period; and
   calculating the shelf life of the pharmaceutical according to the complete numerical analysis data in the complete experimental period of a stability test.

26. The method of integrated pharmaceutical manufacturing and research and development numerical analysis according to claim 25, wherein the stability test analysis procedure further comprises:
   outputting the complete numerical analysis data after obtaining by summarization the complete numerical analysis data;
   generating at least one of the second backup file and a report file according to the complete numerical analysis data; and
   receiving the second backup file as the input file when a user logs in another time, so as to calculate the shelf life of the pharmaceutical according to the complete numerical analysis data in the second backup file.

27. The method of integrated pharmaceutical manufacturing and research and development numerical analysis according to claim 24, wherein the stability test analysis procedure comprises:
   receiving the input file having a complete numerical analysis data in a complete experimental period of a stability test via the user interface, and using the input file as the input file; and
   calculating the shelf life of the pharmaceutical according to the complete numerical analysis data in the received input file.

28. The method of integrated pharmaceutical manufacturing and research and development numerical analysis according to claim 25, wherein the specification data comprises: at least one of individual experimental type data, individual experimental time data, individual storage condition data, and individual packaging condition data of the at least one experimental item.

29. The method of integrated pharmaceutical manufacturing and research and development numerical analysis according to claim 25, wherein the complete numerical analysis data of the pharmaceutical in the complete experimental period is associated with at least one of a selected storage condition and a selected packaging condition.

30. The method of integrated pharmaceutical manufacturing and research and development numerical analysis according to claim 25, wherein the individual numerical analysis data in the at least one experimental period comprises at least one of standard concentration data, sample concentration data, principal component content data, impurity content data, dissolution data, relative standard deviation value data, uniformity data, and test result data of the pharmaceutical.

31. The method of integrated pharmaceutical manufacturing and research and development numerical analysis according to claim 18, wherein the at least one pharmaceutical manufacturing and research and development numerical analysis procedure is an analysis method validation procedure for obtaining at least one characteristic analysis data of the pharmaceuticals according to experimental result data of the pharmaceutical.

32. The method of integrated pharmaceutical manufacturing and research and development numerical analysis according to claim 31, wherein the analysis method validation procedure comprises at least one of the following characteristic analysis steps: a specificity analysis step, a linearity/range analysis step, an accuracy analysis step, a repeatability analysis step, a precision analysis step, a system applicability analysis step, a minimum detectable concentration analysis step, and a minimum quantitative concentration analysis step.

33. The method of integrated pharmaceutical manufacturing and research and development numerical analysis according to claim 32, wherein the analysis method validation procedure further comprises:
   reading at least one of an input file containing analysis item data and data entered online, wherein the analysis item data is used to designate at least one characteristic analysis item to be performed; and
   identifying an attribute of the at least one input file received by the input module, wherein the at least one input file is respectively associated with the at least one characteristic analysis item and assigned to the corresponding one of the at least one characteristic analysis step according to the identified attribute of the at least one input file.

34. A non-transitory computer readable recording medium, configured to store a plurality of instructions configured to, when executed by a computing device, enable the computing device to perform the method of claim 18.

35. The method of integrated pharmaceutical manufacturing and research and development numerical analysis according to claim 18, further comprising receiving, via the user interface, a template file as the at least one input file, and generating a report file as the at least one output file.

* * * * *